United States Patent
Whitman et al.

(10) Patent No.: US 9,113,878 B2
(45) Date of Patent: Aug. 25, 2015

(54) PINION CLIP FOR RIGHT ANGLE LINEAR CUTTER

(75) Inventors: Michael P. Whitman, New Hope, PA (US); John E. Burbank, Ridgefield, CT (US)

(73) Assignee: Covidien LP, Mansfield, MA (US)

(*) Notice: Subject to any disclaimer, the term of this patent is extended or adjusted under 35 U.S.C. 154(b) by 858 days.

(21) Appl. No.: 13/207,529

(22) Filed: Aug. 11, 2011

(65) Prior Publication Data
US 2011/0290054 A1 Dec. 1, 2011

Related U.S. Application Data

(63) Continuation-in-part of application No. 10/094,051, filed on Mar. 8, 2002, now Pat. No. 8,016,855.

(60) Provisional application No. 60/346,656, filed on Jan. 8, 2002.

(51) Int. Cl.
| | | |
|---|---|---|
| *A61B 17/28* | (2006.01) | |
| *A61B 17/072* | (2006.01) | |
| *A61B 17/00* | (2006.01) | |
| *A61B 17/29* | (2006.01) | |

(52) U.S. Cl.
CPC ..... *A61B 17/072* (2013.01); *A61B 2017/00398* (2013.01); *A61B 2017/00464* (2013.01); *A61B 2017/00473* (2013.01); *A61B 2017/00477* (2013.01); *A61B 2017/00526* (2013.01); *A61B 2017/07214* (2013.01); *A61B 2017/2943* (2013.01); *Y10T 74/1987* (2015.01)

(58) Field of Classification Search
CPC .............. F16H 57/0025; A61B 17/072; A61B 2017/00398; A61B 2017/00477; A61B 2017/00526; A61B 2017/2943; A61B 2017/00464; A61B 2017/07214; A61B 2017/00473; Y10T 74/1987
USPC ............. 403/1, 242, 274, 276, 280, 282, 291, 403/292, 297, 300, 315, 316, 317, 326, 356, 403/357, 359.5, 379.6, 397
See application file for complete search history.

(56) References Cited

U.S. PATENT DOCUMENTS

| | | |
|---|---|---|
| 1,798,902 A | 3/1931 | Raney |
| 1,881,250 A | 10/1932 | Tomlinson |
| 2,031,682 A | 2/1936 | Wappler et al. |
| 2,174,219 A | 9/1939 | Balma |
| 2,246,647 A | 6/1941 | Vancura |
| 2,419,045 A | 4/1947 | Whittaker |
| 2,725,628 A | 12/1955 | O'Neilly et al. |
| 3,079,606 A | 3/1963 | Bobrov et al. |
| 3,120,845 A | 2/1964 | Horner |

(Continued)

FOREIGN PATENT DOCUMENTS

| | | |
|---|---|---|
| DE | 2330182 | 1/1975 |
| DE | 29 03 159 | 7/1980 |

(Continued)

*Primary Examiner* — Victor MacArthur

(57) ABSTRACT

Coupling assemblies are provided for maintaining a secure connection between surgical devices utilizing a shaft-and-pinion configuration and powered drive shafts. The coupling assemblies include a clip to be disposed without or within a pinion for receiving and securing a drive shaft member. The coupling assemblies are designed to maximize restriction of movement between the drive shaft and clip, but avoid impeding the rotational motion of a pinion.

7 Claims, 15 Drawing Sheets

(56) References Cited

U.S. PATENT DOCUMENTS

| | | |
|---|---|---|
| 3,193,165 A | 7/1965 | Akhalaya et al. |
| 3,252,643 A | 5/1966 | Strekopytov et al. |
| 3,253,643 A | 5/1966 | Gudheim |
| 3,256,875 A | 6/1966 | Tsepelev et al. |
| 3,275,211 A | 9/1966 | Hirsch et al. |
| 3,315,863 A | 4/1967 | O'Dea |
| 3,317,105 A | 5/1967 | Astafiev et al. |
| 3,369,425 A * | 2/1968 | Runkle et al. ............... 403/357 |
| 3,388,847 A | 6/1968 | Kasulin et al. |
| 3,490,576 A | 1/1970 | Alessi et al. |
| 3,490,675 A | 1/1970 | Green et al. |
| 3,494,533 A | 2/1970 | Green et al. |
| 3,499,591 A | 3/1970 | Green |
| 3,552,626 A | 1/1971 | Astafiev et al. |
| 3,558,165 A * | 1/1971 | Lundergan ................... 403/357 |
| 3,561,799 A * | 2/1971 | Hutchinson ................. 403/356 |
| 3,568,659 A | 3/1971 | Karnegis |
| 3,589,589 A | 6/1971 | Akopov |
| 3,593,903 A | 7/1971 | Astafiev et al. |
| 3,618,842 A | 11/1971 | Bryan |
| 3,638,652 A | 2/1972 | Kelley |
| 3,643,851 A | 2/1972 | Green et al. |
| 3,662,939 A | 5/1972 | Bryan |
| 3,675,688 A | 7/1972 | Bryan et al. |
| 3,692,224 A | 9/1972 | Astafiev et al. |
| 3,717,294 A | 2/1973 | Green |
| 3,735,762 A | 5/1973 | Bryan et al. |
| 3,777,538 A | 12/1973 | Weatherly et al. |
| 3,788,303 A | 1/1974 | Hall |
| 3,795,034 A | 3/1974 | Strekopytov et al. |
| 3,815,476 A | 6/1974 | Green et al. |
| 3,819,100 A | 6/1974 | Noiles et al. |
| 3,837,555 A | 9/1974 | Green |
| 3,844,289 A | 10/1974 | Noiles et al. |
| 3,858,577 A | 1/1975 | Bass et al. |
| 3,859,986 A | 1/1975 | Okada et al. |
| 3,882,854 A | 5/1975 | Hulka et al. |
| 3,892,228 A | 7/1975 | Mitsui |
| 3,935,981 A | 2/1976 | Akopov et al. |
| 3,949,924 A | 4/1976 | Green |
| 3,952,748 A | 4/1976 | Kaliher et al. |
| RE28,932 E | 8/1976 | Noiles et al. |
| 4,014,492 A | 3/1977 | Rothfuss |
| 4,027,510 A | 6/1977 | Hiltebrandt |
| 4,060,089 A | 11/1977 | Noiles |
| 4,064,881 A | 12/1977 | Meredith |
| 4,071,029 A | 1/1978 | Richmond et al. |
| 4,085,756 A | 4/1978 | Weaver |
| 4,086,926 A | 5/1978 | Green et al. |
| 4,092,986 A | 6/1978 | Schneiderman |
| 4,111,206 A | 9/1978 | Vishnevsky et al. |
| 4,169,476 A | 10/1979 | Hiltebrandt |
| 4,198,960 A | 4/1980 | Utsugi |
| 4,198,982 A | 4/1980 | Fortner et al. |
| 4,202,479 A | 5/1980 | Razgulov et al. |
| 4,202,480 A | 5/1980 | Annett |
| 4,207,873 A | 6/1980 | Kruy |
| 4,207,898 A | 6/1980 | Becht |
| 4,244,372 A | 1/1981 | Kapitanov et al. |
| 4,261,244 A | 4/1981 | Becht et al. |
| 4,273,111 A | 6/1981 | Tsukaya |
| 4,273,129 A | 6/1981 | Boebel |
| 4,286,585 A | 9/1981 | Ogawa |
| 4,286,598 A | 9/1981 | Kapitanov et al. |
| 4,289,131 A | 9/1981 | Mueller |
| 4,289,133 A | 9/1981 | Rothfuss |
| 4,296,881 A | 10/1981 | Lee |
| 4,304,236 A | 12/1981 | Conta et al. |
| 4,310,115 A | 1/1982 | Inoue |
| 4,319,576 A | 3/1982 | Rothfuss |
| 4,325,377 A | 4/1982 | Boebel |
| 4,334,539 A | 6/1982 | Childs et al. |
| 4,349,028 A | 9/1982 | Green |
| 4,351,466 A | 9/1982 | Noiles |
| 4,354,628 A | 10/1982 | Green |
| 4,367,729 A | 1/1983 | Ogiu |
| 4,379,457 A | 4/1983 | Gravener et al. |
| 4,383,634 A | 5/1983 | Green |
| 4,391,401 A | 7/1983 | Moshofsky |
| 4,402,311 A | 9/1983 | Hattori |
| 4,402,445 A | 9/1983 | Green |
| 4,429,695 A | 2/1984 | Green |
| 4,442,964 A | 4/1984 | Becht |
| 4,445,509 A | 5/1984 | Auth |
| 4,445,892 A | 5/1984 | Hussein et al. |
| 4,448,188 A | 5/1984 | Loeb |
| 4,461,305 A | 7/1984 | Cibley |
| 4,473,077 A | 9/1984 | Noiles et al. |
| 4,476,863 A | 10/1984 | Kanshin et al. |
| 4,485,811 A | 12/1984 | Chernousov |
| 4,485,817 A | 12/1984 | Swiggett |
| 4,487,270 A | 12/1984 | Huber |
| 4,488,523 A | 12/1984 | Shichman |
| 4,489,724 A | 12/1984 | Amegger |
| 4,489,875 A | 12/1984 | Crawford et al. |
| 4,494,057 A | 1/1985 | Hotta |
| 4,494,549 A | 1/1985 | Namba et al. |
| 4,499,895 A | 2/1985 | Takayama |
| 4,505,272 A | 3/1985 | Utyamyshev et al. |
| 4,505,414 A | 3/1985 | Filipi |
| 4,506,670 A | 3/1985 | Crossley |
| 4,506,671 A | 3/1985 | Green |
| 4,513,746 A | 4/1985 | Aranyi et al. |
| 4,519,532 A | 5/1985 | Foslien |
| 4,520,817 A | 6/1985 | Green |
| 4,527,724 A | 7/1985 | Chow et al. |
| 4,534,352 A | 8/1985 | Korthoff |
| 4,534,420 A | 8/1985 | Goldelius |
| 4,535,773 A | 8/1985 | Yoon |
| 4,559,928 A | 12/1985 | Takayama |
| 4,566,620 A | 1/1986 | Green et al. |
| 4,573,468 A | 3/1986 | Conta et al. |
| 4,573,622 A | 3/1986 | Green et al. |
| 4,574,806 A | 3/1986 | McCarthy |
| 4,576,167 A | 3/1986 | Noiles |
| 4,589,412 A | 5/1986 | Kensey |
| 4,589,416 A | 5/1986 | Green |
| 4,589,582 A | 5/1986 | Bilotti |
| 4,591,085 A | 5/1986 | Di Giovanni |
| 4,592,354 A | 6/1986 | Rothfuss |
| 4,593,679 A | 6/1986 | Collins |
| 4,603,693 A | 8/1986 | Conta et al. |
| 4,605,001 A | 8/1986 | Rothfuss et al. |
| 4,606,343 A | 8/1986 | Conta et al. |
| 4,607,638 A | 8/1986 | Crainich |
| 4,610,383 A | 9/1986 | Rothfuss et al. |
| D286,567 S | 11/1986 | Lichtman et al. |
| 4,631,052 A | 12/1986 | Kensey |
| 4,633,861 A | 1/1987 | Chow et al. |
| 4,633,874 A | 1/1987 | Chow et al. |
| 4,643,190 A | 2/1987 | Heimberger |
| 4,644,952 A | 2/1987 | Patipa et al. |
| 4,646,745 A | 3/1987 | Noiles |
| 4,655,673 A | 4/1987 | Hawkes |
| 4,657,017 A | 4/1987 | Sorochenko |
| 4,664,305 A | 5/1987 | Blake, III et al. |
| 4,667,673 A | 5/1987 | Li |
| 4,669,471 A | 6/1987 | Hayashi |
| 4,671,445 A | 6/1987 | Barker et al. |
| 4,672,961 A | 6/1987 | Davies |
| 4,674,515 A | 6/1987 | Andou et al. |
| 4,688,555 A | 8/1987 | Wardle |
| 4,696,667 A | 9/1987 | Masch |
| 4,700,703 A | 10/1987 | Resnick et al. |
| 4,703,887 A | 11/1987 | Clanton et al. |
| 4,705,038 A | 11/1987 | Sjostrom et al. |
| 4,708,141 A | 11/1987 | Inoue et al. |
| 4,714,187 A | 12/1987 | Green |
| 4,715,502 A | 12/1987 | Salmon |
| 4,728,020 A | 3/1988 | Green et al. |
| 4,732,156 A | 3/1988 | Nakamura |
| 4,733,118 A | 3/1988 | Mihalko |
| 4,742,815 A | 5/1988 | Ninan et al. |
| 4,752,024 A | 6/1988 | Green et al. |

(56) References Cited

U.S. PATENT DOCUMENTS

| | | |
|---|---|---|
| 4,754,909 A | 7/1988 | Barker et al. |
| 4,756,309 A | 7/1988 | Sachse et al. |
| 4,760,840 A | 8/1988 | Fournier, Jr. et al. |
| 4,763,669 A | 8/1988 | Jaeger |
| 4,767,044 A | 8/1988 | Green |
| 4,771,774 A | 9/1988 | Simpson et al. |
| 4,776,506 A | 10/1988 | Green |
| 4,781,186 A | 11/1988 | Simpson et al. |
| 4,784,137 A | 11/1988 | Kulik et al. |
| 4,789,090 A | 12/1988 | Blake, III |
| 4,796,793 A | 1/1989 | Smith et al. |
| 4,805,823 A | 2/1989 | Rothfuss |
| 4,815,469 A | 3/1989 | Cohen et al. |
| 4,817,847 A | 4/1989 | Redtenbacher et al. |
| 4,819,632 A | 4/1989 | Davies |
| 4,819,853 A | 4/1989 | Green |
| 4,841,888 A | 6/1989 | Mills et al. |
| 4,848,637 A | 7/1989 | Pruitt |
| 4,858,608 A | 8/1989 | McQuilkin |
| 4,863,088 A | 9/1989 | Redmond et al. |
| 4,867,158 A | 9/1989 | Sugg |
| 4,869,415 A | 9/1989 | Fox |
| 4,873,977 A | 10/1989 | Avant et al. |
| 4,887,599 A | 12/1989 | Muller |
| 4,887,612 A | 12/1989 | Esser et al. |
| 4,890,602 A | 1/1990 | Hake |
| 4,892,244 A | 1/1990 | Fox et al. |
| 4,893,613 A | 1/1990 | Hake |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,919,152 A | 4/1990 | Ger |
| 4,928,699 A | 5/1990 | Sasai |
| 4,930,494 A | 6/1990 | Takehana et al. |
| 4,932,960 A | 6/1990 | Green et al. |
| 4,936,845 A | 6/1990 | Stevens |
| 4,941,454 A | 7/1990 | Wood et al. |
| 4,941,623 A | 7/1990 | Pruitt |
| 4,944,093 A | 7/1990 | Falk |
| 4,944,443 A | 7/1990 | Oddsen et al. |
| 4,955,882 A | 9/1990 | Hakky |
| 4,955,959 A | 9/1990 | Tompkins et al. |
| 4,957,499 A | 9/1990 | Lipatov et al. |
| 4,962,877 A | 10/1990 | Hervas |
| 4,976,688 A | 12/1990 | Rosenblum |
| 4,976,710 A | 12/1990 | Mackin |
| 4,977,900 A | 12/1990 | Fehling et al. |
| 4,978,049 A | 12/1990 | Green |
| 4,982,726 A | 1/1991 | Taira |
| 4,991,764 A | 2/1991 | Mericle |
| 4,994,060 A | 2/1991 | Rink et al. |
| 4,995,877 A | 2/1991 | Ams et al. |
| 5,005,749 A | 4/1991 | Aranyi |
| 5,018,657 A | 5/1991 | Pedlick et al. |
| 5,031,814 A | 7/1991 | Tompkins et al. |
| 5,040,715 A | 8/1991 | Green et al. |
| 5,059,203 A | 10/1991 | Husted |
| 5,065,929 A | 11/1991 | Schulze et al. |
| D322,143 S | 12/1991 | Spreckelmeier |
| 5,071,430 A | 12/1991 | de Salis et al. |
| 5,077,506 A | 12/1991 | Krause |
| 5,100,041 A | 3/1992 | Storace |
| 5,100,042 A | 3/1992 | Gravener et al. |
| 5,104,025 A | 4/1992 | Main et al. |
| 5,108,391 A | 4/1992 | Flachenecker et al. |
| 5,114,065 A | 5/1992 | Storace |
| 5,119,983 A | 6/1992 | Green et al. |
| 5,129,570 A | 7/1992 | Schulze et al. |
| 5,133,359 A | 7/1992 | Kedem |
| 5,133,713 A | 7/1992 | Huang et al. |
| 5,137,198 A | 8/1992 | Nobis et al. |
| 5,139,513 A | 8/1992 | Segato |
| 5,156,315 A | 10/1992 | Green et al. |
| 5,157,837 A | 10/1992 | Rose |
| 5,158,222 A | 10/1992 | Green |
| 5,170,925 A | 12/1992 | Madden et al. |
| 5,171,247 A | 12/1992 | Hughett et al. |
| 5,171,251 A | 12/1992 | Bregen et al. |
| 5,173,133 A | 12/1992 | Morin et al. |
| 5,192,292 A | 3/1993 | Cezana et al. |
| 5,197,649 A | 3/1993 | Bessler et al. |
| 5,201,325 A | 4/1993 | McEwen et al. |
| 5,201,750 A | 4/1993 | Hocherl et al. |
| 5,205,459 A | 4/1993 | Brinkerhoff et al. |
| 5,207,691 A | 5/1993 | Nardella |
| 5,207,697 A | 5/1993 | Carusillo et al. |
| 5,217,003 A | 6/1993 | Wilk |
| 5,217,460 A | 6/1993 | Knoepfler |
| 5,219,111 A | 6/1993 | Bilotti et al. |
| 5,221,279 A | 6/1993 | Cook et al. |
| 5,224,951 A | 7/1993 | Freitas |
| 5,226,426 A | 7/1993 | Yoon |
| 5,237,884 A | 8/1993 | Seto |
| 5,243,967 A | 9/1993 | Hibino |
| 5,249,583 A | 10/1993 | Mallaby |
| 5,253,793 A | 10/1993 | Green |
| 5,254,117 A | 10/1993 | Rigby et al. |
| 5,258,004 A | 11/1993 | Bales et al. |
| 5,258,007 A | 11/1993 | Spetzler et al. |
| 5,258,008 A | 11/1993 | Wilk |
| 5,261,877 A | 11/1993 | Fine et al. |
| 5,267,997 A | 12/1993 | Farin et al. |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,275,609 A | 1/1994 | Pingleton et al. |
| 5,279,565 A | 1/1994 | Klein et al. |
| 5,285,945 A | 2/1994 | Brinkerhoff et al. |
| 5,289,963 A | 3/1994 | McGarry et al. |
| 5,290,299 A | 3/1994 | Fain et al. |
| 5,290,303 A | 3/1994 | Pingleton et al. |
| 5,292,053 A | 3/1994 | Bilotti et al. |
| 5,295,990 A | 3/1994 | Levin |
| 5,300,087 A | 4/1994 | Knoepfler |
| 5,307,976 A | 5/1994 | Olson et al. |
| 5,312,023 A | 5/1994 | Green et al. |
| 5,312,434 A | 5/1994 | Crainich |
| 5,314,436 A | 5/1994 | Wilk |
| 5,318,221 A | 6/1994 | Green et al. |
| 5,320,627 A | 6/1994 | Sorensen et al. |
| 5,322,055 A | 6/1994 | Davison et al. |
| 5,324,288 A | 6/1994 | Billings et al. |
| 5,324,300 A | 6/1994 | Elias et al. |
| 5,326,013 A | 7/1994 | Green et al. |
| 5,330,471 A | 7/1994 | Eggers |
| 5,330,486 A | 7/1994 | Wilk |
| 5,333,772 A | 8/1994 | Rothfuss et al. |
| 5,333,773 A | 8/1994 | Main et al. |
| 5,336,229 A | 8/1994 | Noda |
| 5,342,299 A | 8/1994 | Snoke et al. |
| 5,342,381 A | 8/1994 | Tidemand |
| 5,342,382 A | 8/1994 | Brinkerhoff et al. |
| 5,344,420 A | 9/1994 | Hilal et al. |
| 5,350,104 A | 9/1994 | Main et al. |
| 5,352,222 A | 10/1994 | Rydell |
| 5,352,223 A | 10/1994 | McBrayer et al. |
| 5,352,235 A | 10/1994 | Koros et al. |
| 5,354,266 A | 10/1994 | Snoke |
| 5,356,408 A | 10/1994 | Rydell |
| 5,358,506 A | 10/1994 | Green et al. |
| 5,364,001 A | 11/1994 | Bryan |
| 5,364,409 A | 11/1994 | Kuwabara et al. |
| 5,366,133 A | 11/1994 | Geiste |
| 5,366,476 A | 11/1994 | Noda |
| 5,368,015 A | 11/1994 | Wilk |
| 5,368,607 A | 11/1994 | Freitas |
| 5,380,321 A | 1/1995 | Yoon |
| 5,383,880 A | 1/1995 | Hooven |
| 5,389,098 A | 2/1995 | Tsuruta et al. |
| 5,391,156 A | 2/1995 | Hildwein et al. |

(56) References Cited

U.S. PATENT DOCUMENTS

| | | |
|---|---|---|
| 5,392,978 A | 2/1995 | Velez et al. |
| 5,395,030 A | 3/1995 | Kuramoto et al. |
| 5,395,033 A | 3/1995 | Byrne et al. |
| 5,395,369 A | 3/1995 | McBrayer et al. |
| 5,396,900 A | 3/1995 | Slater et al. |
| 5,397,046 A | 3/1995 | Savage et al. |
| 5,400,267 A | 3/1995 | Denen et al. |
| D357,535 S | 4/1995 | Grant et al. |
| 5,403,312 A | 4/1995 | Yates et al. |
| 5,403,326 A | 4/1995 | Harrison et al. |
| 5,403,327 A | 4/1995 | Thornton et al. |
| 5,405,344 A | 4/1995 | Williamson et al. |
| 5,411,508 A | 5/1995 | Bessler et al. |
| 5,413,267 A | 5/1995 | Solyntjes et al. |
| 5,413,268 A | 5/1995 | Green et al. |
| 5,415,334 A | 5/1995 | Williamson et al. |
| 5,425,705 A | 6/1995 | Evard et al. |
| 5,425,738 A | 6/1995 | Gustafson et al. |
| 5,425,745 A | 6/1995 | Green et al. |
| 5,431,322 A | 7/1995 | Green et al. |
| 5,431,645 A | 7/1995 | Smith et al. |
| 5,433,721 A | 7/1995 | Hooven et al. |
| 5,437,636 A | 8/1995 | Snoke et al. |
| 5,437,684 A | 8/1995 | Calabrese et al. |
| 5,441,507 A | 8/1995 | Wilk |
| 5,443,198 A | 8/1995 | Viola et al. |
| 5,447,265 A | 9/1995 | Vidal et al. |
| 5,454,825 A | 10/1995 | Van Leeuwen et al. |
| 5,456,684 A | 10/1995 | Schmidt et al. |
| 5,460,182 A | 10/1995 | Goodman et al. |
| 5,464,404 A | 11/1995 | Abela et al. |
| 5,465,894 A | 11/1995 | Clark et al. |
| 5,467,911 A | 11/1995 | Tsuruta et al. |
| 5,468,250 A | 11/1995 | Paraschac et al. |
| 5,472,132 A | 12/1995 | Savage et al. |
| 5,474,223 A | 12/1995 | Viola et al. |
| 5,476,206 A | 12/1995 | Green et al. |
| 5,482,054 A | 1/1996 | Slater et al. |
| 5,482,197 A | 1/1996 | Green et al. |
| 5,485,947 A | 1/1996 | Olson et al. |
| 5,487,499 A | 1/1996 | Sorrentino et al. |
| 5,487,500 A | 1/1996 | Knodel et al. |
| 5,496,269 A | 3/1996 | Snoke |
| 5,496,317 A | 3/1996 | Goble et al. |
| 5,514,134 A | 5/1996 | Rydell et al. |
| 5,518,163 A | 5/1996 | Hooven |
| 5,518,164 A | 5/1996 | Hooven |
| 5,520,634 A | 5/1996 | Fox et al. |
| 5,524,180 A | 6/1996 | Wang et al. |
| 5,527,313 A | 6/1996 | Scott et al. |
| 5,529,235 A | 6/1996 | Boiarski et al. |
| 5,531,687 A | 7/1996 | Snoke et al. |
| 5,533,661 A | 7/1996 | Main et al. |
| 5,535,937 A | 7/1996 | Boiarski et al. |
| 5,549,565 A | 8/1996 | Ryan et al. |
| 5,553,765 A | 9/1996 | Knodel et al. |
| 5,554,169 A | 9/1996 | Green et al. |
| 5,562,677 A | 10/1996 | Hildwein et al. |
| 5,562,702 A | 10/1996 | Huitema et al. |
| 5,569,274 A | 10/1996 | Rapacki et al. |
| 5,569,289 A | 10/1996 | Yoon |
| 5,571,116 A | 11/1996 | Bolanos et al. |
| 5,573,543 A | 11/1996 | Akopov et al. |
| 5,578,052 A | 11/1996 | Koros et al. |
| 5,580,067 A | 12/1996 | Hamblin et al. |
| 5,582,611 A | 12/1996 | Tsukagoshii et al. |
| 5,584,425 A | 12/1996 | Savage et al. |
| 5,588,579 A | 12/1996 | Schnut et al. |
| 5,591,186 A | 1/1997 | Wurster et al. |
| 5,591,196 A | 1/1997 | Marin et al. |
| 5,597,107 A | 1/1997 | Knodel et al. |
| 5,599,347 A | 2/1997 | Hart et al. |
| 5,603,443 A | 2/1997 | Clark et al. |
| 5,607,094 A | 3/1997 | Clark et al. |
| 5,609,285 A | 3/1997 | Grant et al. |
| 5,609,560 A | 3/1997 | Ichikawa et al. |
| 5,618,303 A | 4/1997 | Marlow et al. |
| 5,618,307 A | 4/1997 | Donlon et al. |
| 5,626,607 A | 5/1997 | Malecki et al. |
| 5,639,008 A | 6/1997 | Gallagher et al. |
| 5,651,780 A | 7/1997 | Jackson et al. |
| 5,653,374 A | 8/1997 | Young et al. |
| 5,665,100 A | 9/1997 | Yoon |
| 5,667,473 A | 9/1997 | Finn et al. |
| 5,667,478 A | 9/1997 | McFarcin et al. |
| 5,667,517 A | 9/1997 | Hooven |
| 5,667,526 A | 9/1997 | Levin |
| 5,676,674 A | 10/1997 | Bolanos et al. |
| 5,688,269 A | 11/1997 | Newton et al. |
| 5,692,668 A | 12/1997 | Schulze et al. |
| 5,693,031 A | 12/1997 | Ryan et al. |
| 5,702,408 A | 12/1997 | Wales et al. |
| 5,709,335 A | 1/1998 | Heck |
| 5,711,472 A | 1/1998 | Bryan |
| 5,725,536 A | 3/1998 | Oberlin et al. |
| 5,732,871 A | 3/1998 | Clark et al. |
| 5,732,872 A | 3/1998 | Bolduc et al. |
| 5,735,848 A | 4/1998 | Yates et al. |
| 5,735,849 A | 4/1998 | Baden et al. |
| 5,735,861 A | 4/1998 | Peifer et al. |
| 5,741,285 A | 4/1998 | McBrayer et al. |
| 5,749,885 A | 5/1998 | Sjostrom et al. |
| 5,749,893 A | 5/1998 | Vidal et al. |
| 5,752,644 A | 5/1998 | Bolanos et al. |
| 5,758,814 A | 6/1998 | Gallagher et al. |
| 5,762,458 A | 6/1998 | Wang et al. |
| 5,779,130 A | 7/1998 | Alesi et al. |
| 5,782,396 A | 7/1998 | Mastri et al. |
| 5,782,397 A | 7/1998 | Koukline |
| 5,792,135 A | 8/1998 | Madhani et al. |
| 5,792,165 A | 8/1998 | Klieman et al. |
| 5,797,835 A | 8/1998 | Green |
| 5,797,900 A | 8/1998 | Madhani et al. |
| 5,797,944 A | 8/1998 | Nobles et al. |
| 5,807,180 A * | 9/1998 | Knodle et al. ................ 403/357 |
| 5,807,377 A | 9/1998 | Madhani et al. |
| 5,807,402 A | 9/1998 | Yoon |
| 5,814,044 A | 9/1998 | Hooven |
| 5,815,640 A | 9/1998 | Wang et al. |
| 5,817,113 A | 10/1998 | Gifford, III et al. |
| 5,817,119 A | 10/1998 | Klieman et al. |
| 5,823,956 A | 10/1998 | Roth et al. |
| 5,826,776 A | 10/1998 | Schulze et al. |
| 5,829,662 A | 11/1998 | Allen et al. |
| 5,836,503 A | 11/1998 | Ehrenfels et al. |
| 5,846,221 A | 12/1998 | Snoke et al. |
| 5,855,583 A | 1/1999 | Wang et al. |
| 5,855,590 A | 1/1999 | Malecki et al. |
| 5,857,996 A | 1/1999 | Snoke |
| 5,860,953 A | 1/1999 | Snoke et al. |
| 5,868,760 A | 2/1999 | McGuckin, Jr. |
| 5,871,471 A | 2/1999 | Ryan et al. |
| 5,878,193 A | 3/1999 | Wang et al. |
| 5,881,943 A | 3/1999 | Heck et al. |
| 5,893,875 A | 4/1999 | O'Connor et al. |
| 5,897,562 A | 4/1999 | Bolanos et al. |
| 5,901,895 A | 5/1999 | Heaton et al. |
| 5,907,664 A | 5/1999 | Wang et al. |
| 5,913,842 A | 6/1999 | Boyd et al. |
| 5,915,616 A | 6/1999 | Viola et al. |
| 5,925,055 A | 7/1999 | Adrian et al. |
| 5,931,848 A | 8/1999 | Saadat |
| 5,947,363 A | 9/1999 | Bolduc et al. |
| 5,951,549 A | 9/1999 | Richardson et al. |
| 5,954,259 A | 9/1999 | Viola et al. |
| 5,957,363 A | 9/1999 | Heck |
| 5,957,882 A | 9/1999 | Nita et al. |
| 5,957,884 A | 9/1999 | Hooven |
| 5,976,159 A | 11/1999 | Bolduc et al. |
| 5,984,919 A | 11/1999 | Hilal et al. |
| 5,989,215 A | 11/1999 | Delmotte et al. |
| 5,993,378 A | 11/1999 | Lemelson |
| 5,993,454 A | 11/1999 | Longo |
| 5,997,510 A | 12/1999 | Schwemberger |

(56) References Cited

U.S. PATENT DOCUMENTS

| | | | |
|---|---|---|---|
| 6,001,108 | A | 12/1999 | Wang et al. |
| 6,004,335 | A | 12/1999 | Vaitekunas et al. |
| 6,007,512 | A | 12/1999 | Hooven |
| 6,007,531 | A | 12/1999 | Snoke et al. |
| 6,010,054 | A | 1/2000 | Johnson et al. |
| 6,010,493 | A | 1/2000 | Snoke |
| 6,017,322 | A | 1/2000 | Snoke et al. |
| 6,017,354 | A | 1/2000 | Culp et al. |
| 6,024,741 | A | 2/2000 | Williamson, IV et al. |
| 6,063,095 | A | 5/2000 | Wang et al. |
| 6,068,627 | A | 5/2000 | Orszulak et al. |
| 6,074,402 | A | 6/2000 | Peifer et al. |
| 6,083,163 | A | 7/2000 | Wegner et al. |
| 6,086,600 | A | 7/2000 | Kortenbach |
| 6,090,120 | A | 7/2000 | Wright et al. |
| 6,098,660 | A * | 8/2000 | Hansen .................. 403/366 |
| 6,099,466 | A | 8/2000 | Sano et al. |
| 6,106,512 | A | 8/2000 | Cochran et al. |
| 6,110,188 | A | 8/2000 | Narciso, Jr. |
| 6,119,913 | A | 9/2000 | Adams et al. |
| 6,126,058 | A | 10/2000 | Adams et al. |
| 6,126,591 | A | 10/2000 | McGarry et al. |
| 6,132,368 | A | 10/2000 | Cooper |
| 6,162,220 | A | 12/2000 | Nezhat |
| 6,165,191 | A | 12/2000 | Shibata et al. |
| 6,174,324 | B1 | 1/2001 | Egan et al. |
| 6,179,837 | B1 | 1/2001 | Hooven |
| 6,193,129 | B1 | 2/2001 | Bittner et al. |
| D438,617 | S | 3/2001 | Cooper et al. |
| 6,201,984 | B1 | 3/2001 | Funda et al. |
| 6,206,903 | B1 | 3/2001 | Ramans |
| D441,076 | S | 4/2001 | Cooper et al. |
| 6,209,773 | B1 | 4/2001 | Bolduc et al. |
| 6,217,591 | B1 | 4/2001 | Egan et al. |
| D441,862 | S | 5/2001 | Cooper et al. |
| 6,231,587 | B1 | 5/2001 | Makower |
| 6,238,414 | B1 | 5/2001 | Griffiths |
| 6,244,809 | B1 | 6/2001 | Wang et al. |
| 6,246,200 | B1 | 6/2001 | Blumenkranz et al. |
| D444,555 | S | 7/2001 | Cooper et al. |
| 6,264,087 | B1 | 7/2001 | Whitman |
| 6,270,508 | B1 | 8/2001 | Klieman |
| 6,309,397 | B1 | 10/2001 | Julian et al. |
| 6,312,435 | B1 | 11/2001 | Wallace et al. |
| 6,315,184 | B1 | 11/2001 | Whitman |
| 6,331,181 | B1 | 12/2001 | Tierney et al. |
| 6,346,072 | B1 | 2/2002 | Cooper |
| 6,348,061 | B1 | 2/2002 | Whitman |
| 6,364,888 | B1 | 4/2002 | Niemeyer et al. |
| 6,368,340 | B2 | 4/2002 | Malecki et al. |
| 6,371,952 | B1 | 4/2002 | Madhani et al. |
| 6,394,998 | B1 | 5/2002 | Wallace et al. |
| 6,398,726 | B1 | 6/2002 | Ramans et al. |
| 6,443,973 | B1 | 9/2002 | Whitman |
| 6,488,197 | B1 | 12/2002 | Whitman |
| 6,491,201 | B1 | 12/2002 | Whitman |
| 6,505,768 | B2 | 1/2003 | Whitman |
| 6,517,565 | B1 | 2/2003 | Whitman et al. |
| 6,533,157 | B1 | 3/2003 | Whitman |
| 6,790,217 | B2 | 9/2004 | Schulze et al. |
| 2001/0016146 | A1* | 8/2001 | Blanchard .................. 403/357 |
| 2001/0016750 | A1 | 8/2001 | Malecki et al. |
| 2001/0031975 | A1 | 10/2001 | Whitman et al. |
| 2002/0032451 | A1 | 3/2002 | Tierney et al. |
| 2002/0032452 | A1 | 3/2002 | Tierney et al. |
| 2002/0042620 | A1 | 4/2002 | Julian et al. |
| 2002/0045888 | A1 | 4/2002 | Ramans et al. |
| 2002/0049454 | A1 | 4/2002 | Whitman et al. |
| 2002/0055795 | A1 | 5/2002 | Niemeyer et al. |
| 2002/0072736 | A1 | 6/2002 | Tierney et al. |
| 2002/0165444 | A1 | 11/2002 | Whitman |
| 2003/0105478 | A1 | 6/2003 | Whitman et al. |
| 2003/0130677 | A1 | 7/2003 | Whitman et al. |
| 2009/0294602 | A1* | 12/2009 | Korczak .................. 248/74.2 |

FOREIGN PATENT DOCUMENTS

| | | |
|---|---|---|
| DE | 2944108 | 10/1980 |
| DE | 31 14 135 | 10/1982 |
| DE | 3114135 | 10/1982 |
| DE | 33 00 768 | 7/1984 |
| DE | 42 13 426 | 10/1992 |
| DE | 4312147 | 10/1992 |
| EP | 41022 | 12/1981 |
| EP | 0 116 220 | 8/1984 |
| EP | 0 121 474 | 10/1984 |
| EP | 0 142 225 | 5/1985 |
| EP | 0 156 774 | 10/1985 |
| EP | 0 203 375 | 12/1986 |
| EP | 0 216 532 | 4/1987 |
| EP | 293123 | 1/1988 |
| EP | 324166 | 7/1989 |
| EP | 324637 | 7/1989 |
| EP | 365153 | 4/1990 |
| EP | 369324 | 5/1990 |
| EP | 373762 | 6/1990 |
| EP | 0 399 701 | 11/1990 |
| EP | 0 514 139 | 11/1992 |
| EP | 0 536 903 | 4/1993 |
| EP | 0 539 762 | 5/1993 |
| EP | 0 552 050 | 7/1993 |
| EP | 0 593 920 | 4/1994 |
| EP | 0 598 579 | 5/1994 |
| EP | 0 621 006 | 10/1994 |
| EP | 630612 | 12/1994 |
| EP | 0 634 144 | 1/1995 |
| EP | 639349 | 2/1995 |
| EP | 679367 | 11/1995 |
| EP | 0 705 571 | 4/1996 |
| EP | 0 648 476 B1 | 1/1998 |
| EP | 552423 | 1/1998 |
| EP | 0 878 169 | 11/1998 |
| EP | 0 947 167 | 10/1999 |
| EP | 0 653 922 | 12/1999 |
| EP | 581400 | 5/2000 |
| EP | 484677 | 7/2000 |
| FR | 2660851 | 10/1991 |
| GB | 1 082 821 | 9/1967 |
| GB | 1352554 | 5/1974 |
| GB | 1452185 | 10/1976 |
| GB | 2048685 | 12/1980 |
| GB | 2165559 | 4/1986 |
| GB | 2180455 | 4/1987 |
| NL | 77 11 347 | 0/1979 |
| NL | 7711347 | 4/1979 |
| RU | 659146 | 4/1979 |
| WO | WO 82/03545 | 10/1982 |
| WO | WO 90/05489 | 5/1990 |
| WO | WO 90/05491 | 5/1990 |
| WO | WO 9006085 | 6/1990 |
| WO | WO 91/07136 | 5/1991 |
| WO | WO 92/16141 | 10/1992 |
| WO | WO 93/08754 | 5/1993 |
| WO | WO 93/14706 | 8/1993 |
| WO | WO 95/35065 | 12/1995 |
| WO | WO 95/18572 | 7/1996 |
| WO | WO 97/12555 | 4/1997 |
| WO | WO 98/14129 | 4/1998 |
| WO | WO 99/20328 | 4/1999 |
| WO | WO 99/58076 | 11/1999 |
| WO | WO 00/72765 | 12/2000 |
| WO | WO 00/72765 A1 | 12/2000 |
| WO | WO 01/03587 | 1/2001 |
| WO | WO 01/08572 | 2/2001 |
| WO | WO 01/17448 | 3/2001 |
| WO | WO 01/35813 | 5/2001 |
| WO | WO 01/62163 | 8/2001 |
| WO | WO 01/91646 A1 | 12/2001 |
| WO | WO 02/058539 | 8/2002 |

\* cited by examiner

PINION CLIP FOR RIGHT ANGLE LINEAR CUTTER

CROSS-REFERENCE TO RELATED APPLICATIONS

This application is a Continuation-in-Part Application claiming the benefit of and priority to U.S. patent application Ser. No. 10/094,051, filed on Mar. 8, 2002 now U.S. Pat. No. 8,016,855, which claims the benefit of and priority to U.S. Provisional Application Ser. No. 60/346,656, filed on Jan. 8, 2002, the entire contents of each of which are incorporated by reference herein.

BACKGROUND

1. Technical Field

The present disclosure relates to electro-mechanical surgical devices and/or systems. Specifically, the present disclosure relates to pinion clips for use in maintaining a secure connection in a pinion-and-shaft configuration of an electro-mechanical surgical device and/or system.

2. Background of Related Art

A number of surgical device manufacturers have developed product lines with proprietary drive systems for operating and/or manipulating the surgical device. In many instances, the drive system includes a drive shaft coupled to a pinion for driving, rotating, and/or articulating an end effector of the surgical device.

Many of the existing coupling configurations between the drive shaft and pinion suffer from too much freedom of movement between the shaft and pinion. As such, many existing coupling configurations have an adverse effect on both the efficiency and control of the electro-mechanical surgical devices.

In order to address the problem of movement between the drive shaft and pinion during operation, a need exists for a more secure assembly of an end effector of the electro-mechanical surgical device to the driving member of the electro-mechanical surgical device.

SUMMARY

The present disclosure relates to pinion clips for use in maintaining a secure connection in a pinion-and-shaft configuration of an electro-mechanical surgical device and/or system.

According to one embodiment of the present invention, a pinion clip for use in a drive shaft and pinion assembly is provided, wherein the pinion defines a longitudinal axis and having an internal bore. The pinion clip includes at least one arm, defining an arm axis, disposed along the longitudinal axis of the pinion and being configured to at least partially project into the internal bore of the pinion. The pinion clip further includes at least one base member, defining a base axis, oriented transverse to the longitudinal axis of the pinion. The pinion clip is positioned on the pinion such that the at least one arm intersects the diameter of the internal bore of the pinion.

The at least one arm may contain at least one goose-neck portion configured to engage a surface of a drive shaft inserted into the bore of the pinion.

The pinion clip may include a collar configured to attach the coupling clip to an outer circumference of the pinion. The collar may be substantially annular. The collar may include at least one deformed portion defining a flat. The collar may be configured for receipt in a receiving surface defined in an outer surface of the pinion. The collar may be a split collar defining opposed ends that project radially inward for engagement with at least one corresponding receiving surface defined in an outer surface of the pinion. The circumference of the collar may be non-continuous.

The pinion clip may further include at least one base post extending from a side edge of the back member in a direction transverse to a plane defined by the backspan, wherein the at least one base post extends beyond the diameter of the internal bore of the pinion when the coupling clip is connected to the pinion.

The pinion clip may contain an aperture for the receipt of a locking pin.

According to another aspect of the present disclosure, a pinion and pinion clip assembly configured for selective coupling with a rotatable drive shaft is provided. The pinion and pinion clip assembly includes a pinion being a substantially cylindrical member, the pinion having proximal and distal ends and defining a longitudinal axis and an internal bore; and a pinion clip configured for connection to the pinion, the pinion clip including at least one base member, defining a base axis, oriented transverse to the longitudinal axis of the pinion, and at least one arm extending from the base member, each arm defining an arm axis disposed at an angle relative to the base axis of the base member, wherein each arm is configured to at least partially project into the internal bore of the pinion. The pinion clip is positioned on the pinion such that the at least one arm intersects the diameter of the internal bore.

The pinion may include at least one pinion groove formed in an outer surface thereof and being configured to receive the at least one arm of the pinion clip.

The at least one arm may contain at least one goose-neck portion configured to project into the internal bore of the pinion.

The pinion clip may include a collar configured to attach the pinion clip to an outer circumference of the pinion. The collar may be substantially annular. The collar may include at least one deformed portion defining a flat.

The pinion may define a receiving surface in an outer surface thereof, and wherein the collar may be configured for disposition in the receiving surface defined in the outer surface of the pinion.

The pinion may define a receiving surface in an outer surface thereof. The collar may be a split collar defining opposed ends that project radially inward for engagement with the receiving surface defined in the outer surface of the pinion.

The pinion clip may further include at least one base post extending from a side edge of the base member in a direction transverse to a plane defined by the base member, wherein the at least one base post extends beyond a diameter of the internal bore of the pinion when the pinion clip is connected to the pinion.

The pinion clip may contain an aperture for the receipt of a locking pin.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
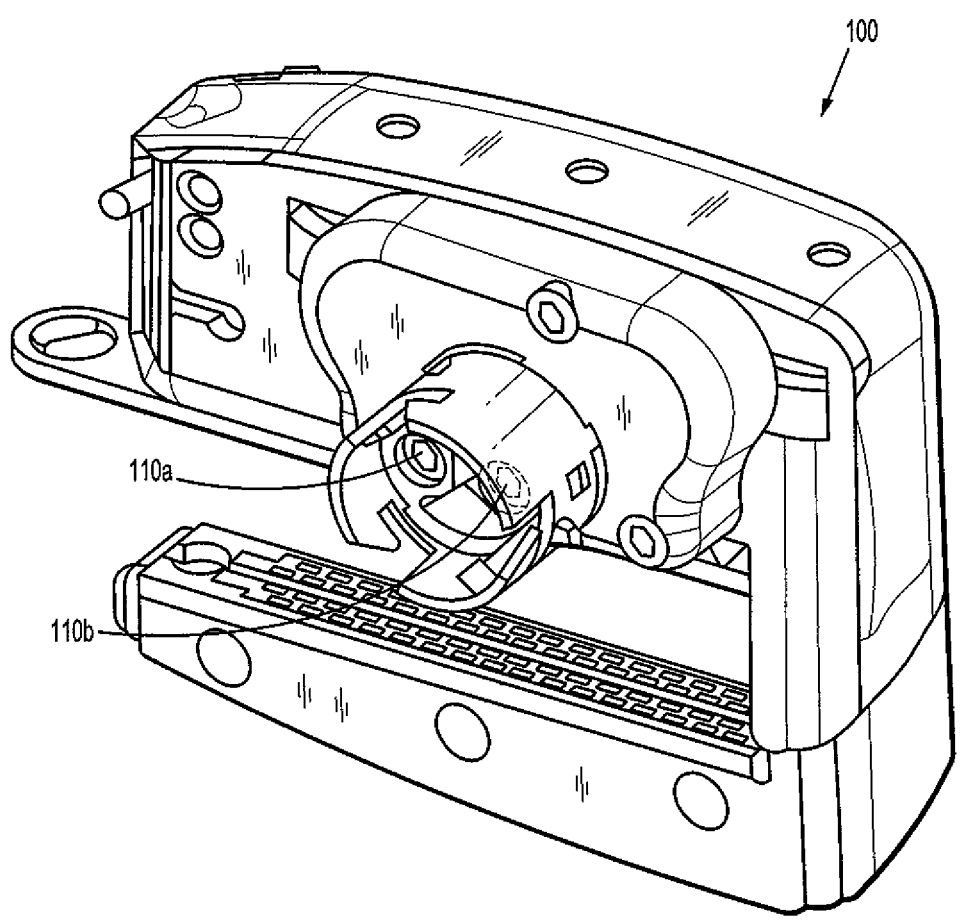
FIG. 1 is a perspective view of a surgical device or end effector of the type driven by a shaft-and-pinion assembly.

Embodiments of the presently disclosed pinion clips for use in electro-mechanical surgical devices are described in detail with reference to the drawings, in which like reference numerals designate identical or corresponding elements in each of the several views.

In most embodiments, a pinion clip is designed such that it is disposed without or within a pinion, and has structure for receiving a drive shaft or other drive member. Certain embodiments of the pinion clips of the present disclosure contain structure for securing the pinion clip within or without the drive or shaft member, such that movement of the drive shaft or member in an axial direction, as well as rotation, relative to a pinion, is inhibited.

Figure 2:
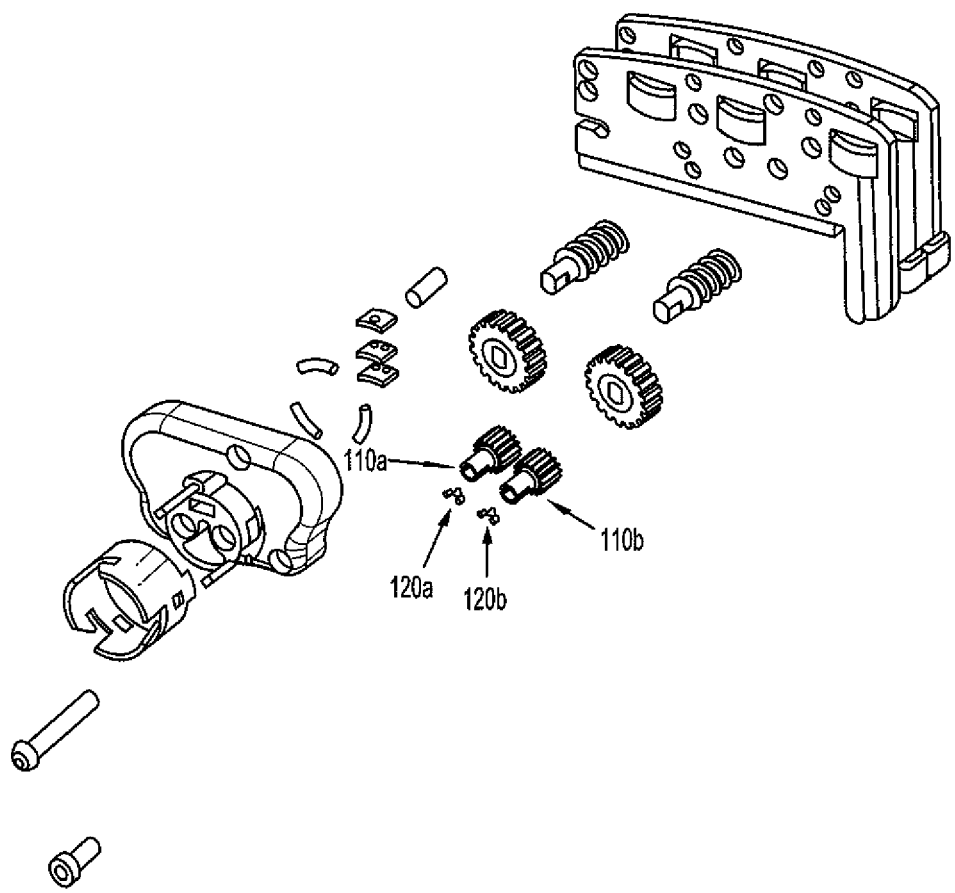
FIG. 2 is an exploded perspective view of the surgical device of FIG. 1, illustrating the relative placement of the pinions within the surgical device.
Figure 3:
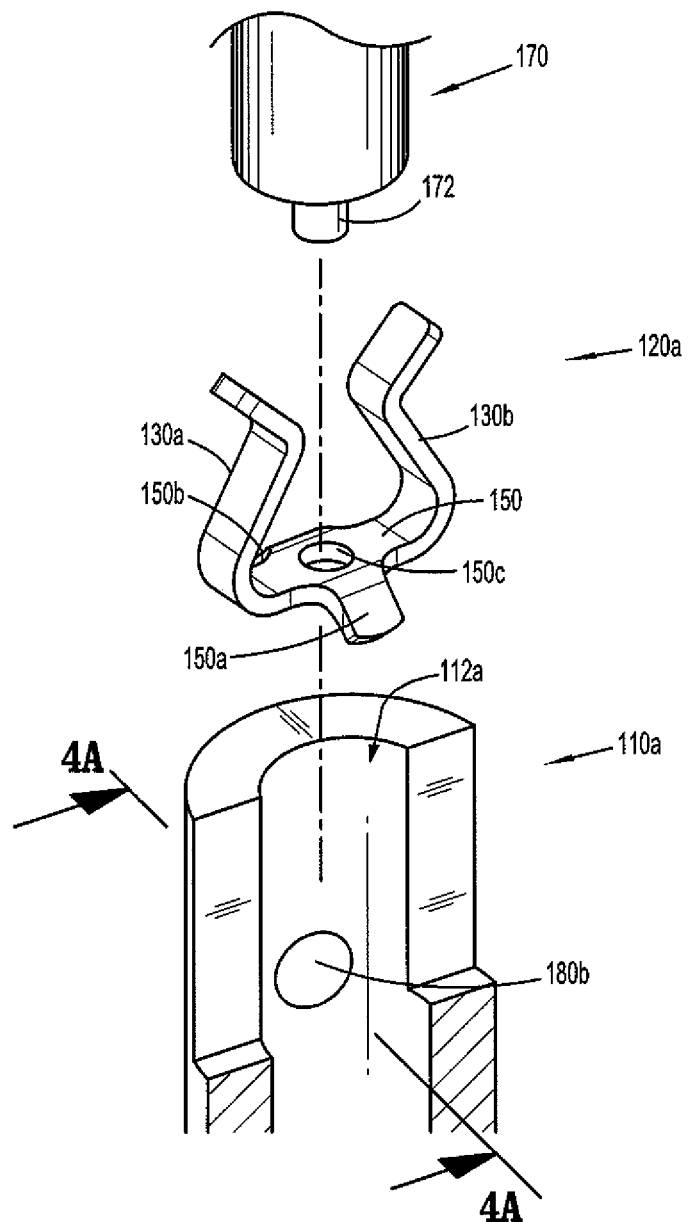
FIG. 3 is a cross-sectional view of one embodiment of the pinion, with the pinion clip aligned for placement within the pinion and the insertion tool readied for application above the pinion clip.

Referring initially to FIG. 1, a surgical device or end effector, generally designated as 100, is shown and is configured to be capable of connection to powered, rotating drive shafts of an electro-mechanical power source (not shown). Surgical device 100 and the drive shafts are coupled to one another by a shaft-and-pinion assembly, wherein the drive shafts are inserted into pinions 110a and 110b, as seen in FIGS. 1 and 2. In use, the drive shafts (not shown) are securely engaged within the pinions 110a and 110b and when turned, actuate components disposed on or in the surgical device 100. It should be noted that pinion 110a is substantially similar to pinion 110b, and this will only be discussed herein to the extent necessary to describe the differences in construction/configuration/operation thereof.

Reference may be made to U.S. patent application Ser. No. 10/094,051 (U.S. Patent Publication No. 2003/0130677), filed on Mar. 8, 2002, entitled "Surgical Device", the entire content of which is incorporated herein by reference, for a detailed discussion of the construction and operation of surgical device 100.

To enhance the secured connection of a drive shaft to a pinion 110a, 110b, pinion clips 120a and 120b are shown to be attached, connected to, or supported on pinions 110a and 110b, respectively. In embodiments, pinion clips 120a, 120b will be formed of a material capable of elastic deformation. However, pinion clips 120a, 120b may be formed of materials that do not deform elastically but rather have a predefined, rigid configuration. In the case of pinion clips 120a, 120b formed of materials capable of elastic deformation, generally when the pinion clips 120a, 120b are engaged by a drive member having a cross-sectional dimension that is larger than a dimension of a span thereof, the pinion clips 120a, 120b will deform elastically and produce a clamping force on the outer surface of the drive member. As such, when drive shafts are inserted into the pinion clips 120a and 120b, the pinion clips 120a, 120b will engage the outer circumference of the drive shafts and enhance the connection between pinions 110a, 110b and respective drive shaft (not shown).

As pinion clips 120a and 120b are substantially similar, reference will hereafter be made solely to pinion clip 120a, but will impliedly apply to pinion 120b as well.

Turning now to FIGS. 3-7B, a pinion clip 120a, in accordance with an embodiment of the present disclosure, is shown in which the pinion clip 120a includes a base member or backspan 150, defining a hole or aperture 150c therein, a pair of pinion clip arms 130a and 130b, extending from opposed longitudinal ends of base member 150, and a pair of base posts 150a and 150b extending from opposed side edges of base member or backspan 150.

As seen in FIGS. 3-7B, backspan 150 defines a plane and base posts 150a, 150b extend from backspan 150 in a direction transverse to the plane defined by backspan 150 so as to extend away from one another. Also as seen in FIGS. 3-7B, pinion clip arms 130a, 130b include a first portion that extends from backspan 150 in a direction transverse to the plane defined by backspan 150 so as to extend towards one another and a second portion, extending from the first portion, in a direction that is away from one another. As such, pinion clip arms 130a, 130b each define a goose-neck portion that extends toward one another.

In embodiments, base posts 150a and 150b are capable of deformation. In this view, pinion clip 120a is connected to pinion 110a by inserting pinion clip 120a into the inner circumference of bore 112a of pinion 110a.

Turning now to FIGS. 4A-4D, cross sectional views of the sequence of placement and securing of pinion clip 120a within the pinion 110a is shown. In order to connect pinion clip 120a to pinion 110a, base posts 150a, 150b are aligned with respective base post holes (only one base post hole 180 being shown in FIG. 3) and pinion clip 120a is advanced into bore 112a of pinion 110a, with the assistance of an insertion tool 170. Pinion clip 120a is inserted into bore 112a of pinion 110a such that base posts 150a, 150b enter bore 112a before pinion clip aims 130a, 130b. In order to facilitate insertion, insertion tool 170 may include a nub or stem 172 extending from a distal surface thereof that is configured and dimensioned to engage the aperture 150c defined in backspan 150.

In accordance with the present disclosure, base posts 150a, 150b define a distance between the tips thereof that is greater than a diameter of bore 112a of pinion 110a. In this manner, base posts 150a, 150b must be flexed toward one another in order to insert pinion clip 120a into bore 112a of pinion 110a. As pinion clip 120a is advanced into bore 112a of pinion 110a until base posts 150a, 150b engage and enter base post holes 180a, 180b.

Figure 4A:
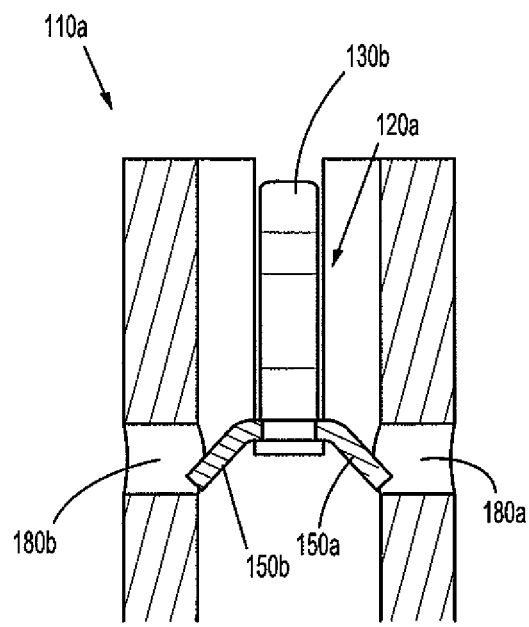
FIG. 4A shows the embodiment of the pinion clip of FIG. 3 in cross-section and placed within a pinion before being secured.

As seen in FIG. 4A, the pinion clip 120a is disposed within the pinion 110a, such that the tips of base posts 150a and 150b rest upon or within base post holes 180a and 180b.

Figure 4B:
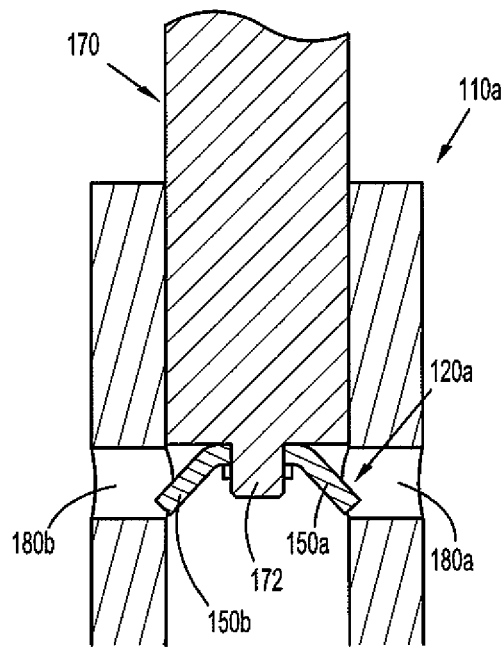
FIG. 4B shows the pinion clip of FIG. 3 in cross-section and disposed within a pinion, and at the initial point of contact with the insertion tool, before the pinion clip is secured within the pinion.

As seen in FIG. 4B, the insertion tool 170 is shown in engagement with pinion clip 120a, such that stem 172 of insertion tool 170 is seated in aperture 150c of backspan 150.

Figure 4C:
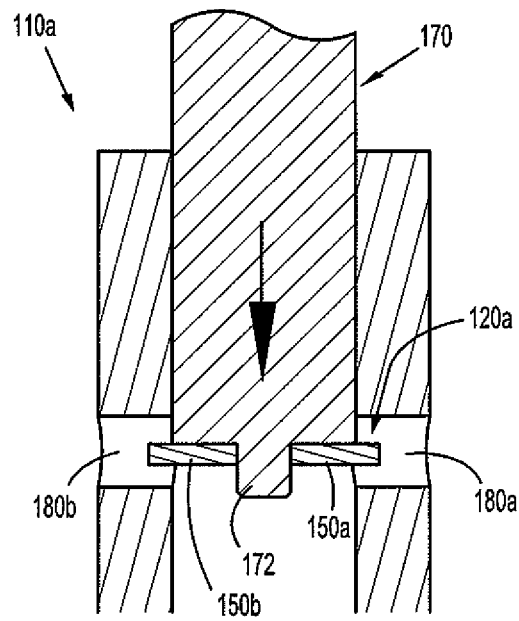
FIG. 4C shows the pinion clip of FIG. 3 in cross-section subject to forces exerted by the insertion tool. The base posts are shown in a resultant deformed state and in contact with base post holes for receiving them.

As seen in FIG. 4C, the insertion tool 170 is shown applying a force on the pinion clip 120a such that the base posts 150a and 150b are defoinied to extend into and better engage pinion holes 180a and 180b.

Figure 4D:
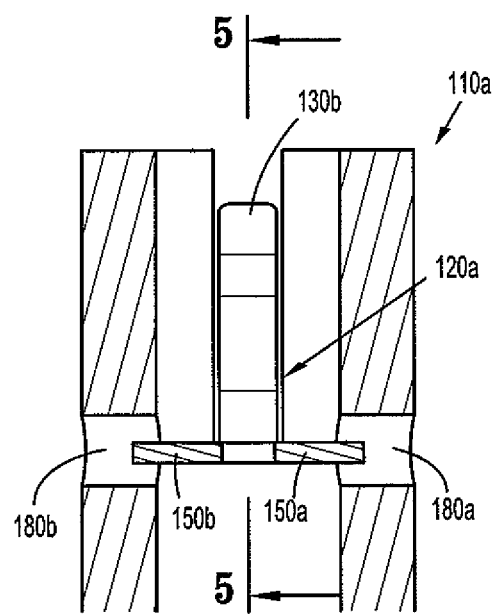
FIG. 4D is a cross-sectional view of the pinion of FIG. 3, showing the final resting position of the pinion clip of that embodiment, with the base posts in secure attachment to the base post holes.

Turning to FIG. 4D, the final resting position of the pinion clip 120a is shown, illustrating the base posts 150a and 150b, in their deformed state, in engagement with the base post holes 180a and 180b such that pinion clip 120a is securely disposed within pinion 110.

The placement of the base posts 150a and 150b in the base post holes 180a and 180b have the dual purpose of preventing movement of the pinion clip 120a in all three axial directions. As so placed, pinion clip arms 130a and 130b engage pinion grooves 114a and 114b in the outer circumference of pinion 110a.

Figure 5:
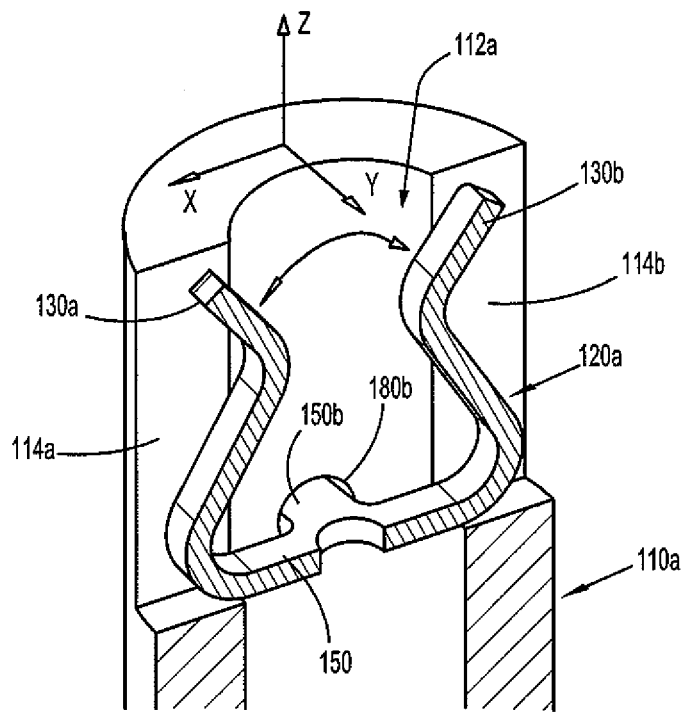
FIG. 5 is a cross-sectional view of the pinion clip of FIG. 3 secured within the pinion.
Figure 6:
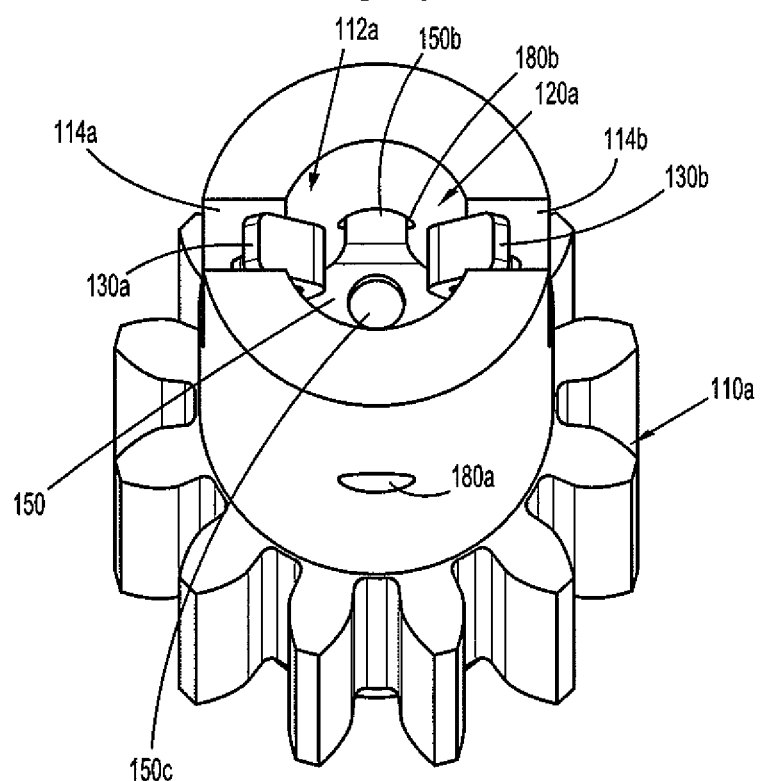
FIG. 6 is a top perspective view of the pinion clip of FIG. 3 secured within the pinion.

As seen in FIGS. 5 and 6, the final placement of the pinion clip 120a is shown. In particular, as seen in FIGS. 5 and 6, backspan 150 rests on ridges or ledges which are formed at the base of pinion grooves 114a, 114b and base posts 150a, 150b are engaged within base post holes 180a, 180b.

Figure 7A:
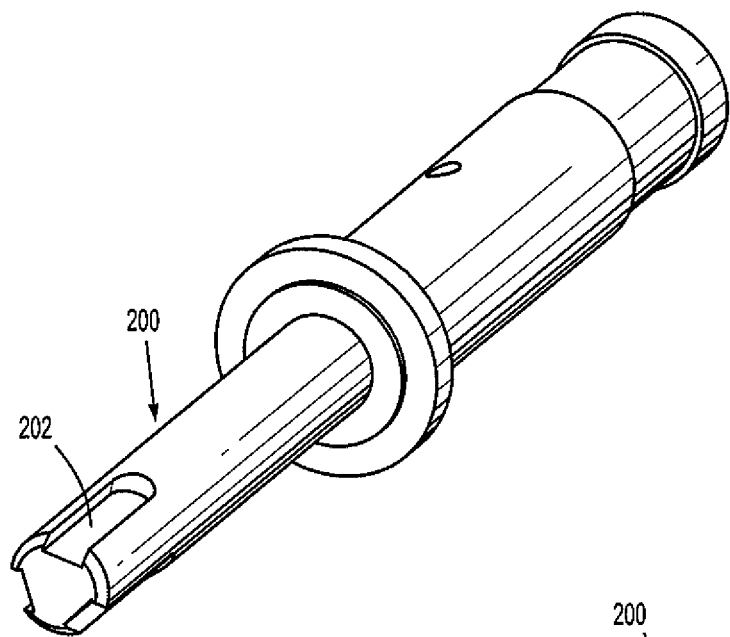
FIG. 7A is a perspective view of the pinion clip of FIG. 3, fully assembled with the pinion and drive shaft.
Figure 7B:
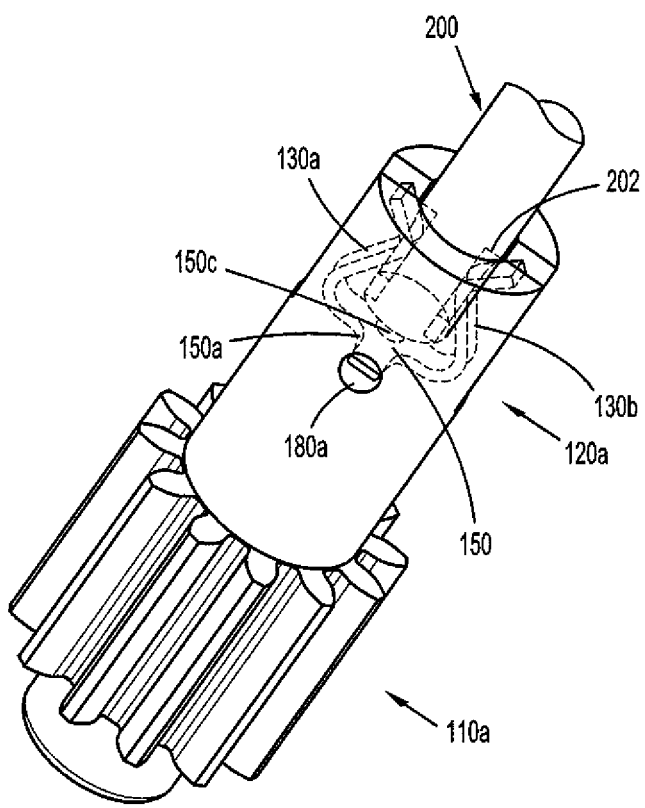
FIG. 7B is a perspective view of the pinion clip of FIG. 3, in full assembly and showing the placement of the pinion clip within the pinion in hidden view.

Turning now to FIGS. 7A and 7B, a drive shaft 200 is shown and as illustrated in FIG. 7B, is shown inserted into pinion 110a and engaged by pinion clip 120a.

As seen in FIG. 7B, the goose-neck portions of pinion clip arms 130a and 130b can be seen engaged against or in contact with an outer surface of drive shaft 200 while in pinion 110a. At least one of pinion clip arms 130a, 130b is in a deflected condition in response to the presence of drive shaft 200 in pinion 110a and between pinion clip arms 130a, 130b. In particular, the goose-neck portion of one of pinion clip arms 130a, 130b will enter and engage a longitudinally extending slot or groove 202 (see FIG. 7A) formed in the outer surface of drive shaft 200 and the goose-neck portion of the other of pinion clip arms 130a, 130b will engage an outer surface of drive shaft 200. A clamping force of the pinion clip arms 130a and 130b creates a secure connection about the drive shaft 200. Due to the engagement of the base posts 150a and 150b (unseen) within the base post holes 180a and 180b (also unseen), pinion clip 110a is prevented from rotation relative to the pinion 110a. As such, a torque or rotation in the drive shaft 200 is transmitted wholly and directly to the pinion 110a.

Figure 8:
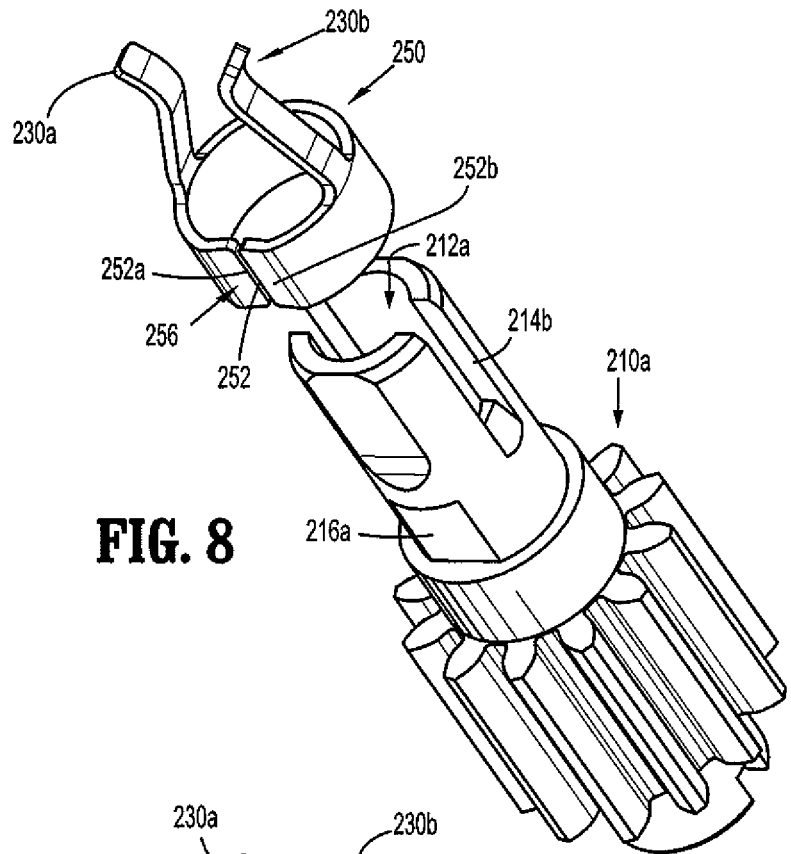
FIG. 8 is a perspective view of an embodiment of a pinion clip including a collar and receiving band, aligned for placement about the pinion.

Turning now to FIG. 8, another embodiment of a pinion clip 220a is shown in which the pinion clip 220a includes a collar 250 for attaching the pinion clip 220a to the pinion 210a. In this embodiment, the pinion clip 220a is disposed on the outer circumference of pinion 210a. As seen in FIG. 8, pinion clip 220a includes a split collar 250 defining an opening 252 for receiving pinion 210a therein and is split 252 at a radial location thereof so as to define a pair of ends 252a, 252b. The ends 252a, 252b of collar 250 are formed radially inward to define a flat 256a.

Pinion clip 210a includes a pair of pinion clip arms 230a, 230b extending from an edge of split collar 250. Pinion clip arms 230a, 230b are substantially similar to pinion clip arms 130a, 130b as described above and will not be described in further detail herein. Pinion clip arms 230a and 230b engage pinion grooves 214a and 214b, respectively, when pinion clip 220a is connected to pinion 210a. When engaged to pinion 210a, flat 256a of collar 250 of pinion clip 220a engages a receiving surface or flat 216a defined in an outer surface of pinion 210a, which prevents at least rotation of pinion clip 220a about a central rotational axis of pinion 210a.

Figure 9:
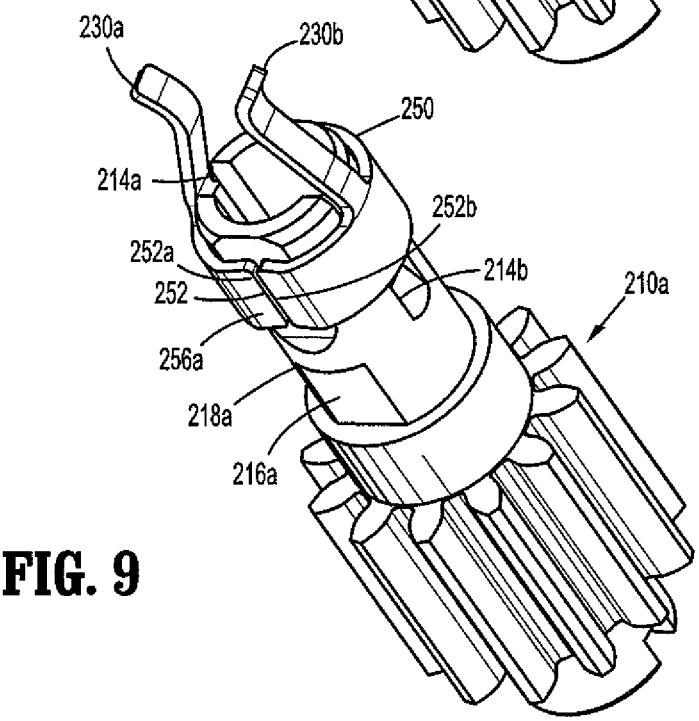
FIG. 9 is a perspective view of the pinion clip of FIG. 8 during placement about the pinion.

FIG. 9 illustrates pinion clip 220a being fitted about pinion 210a. As shown in FIG. 9, flat 256a of pinion clip 220a is aligned for engagement with the receiving surface or flat 216a, and the pinion clip arms 230a and 230b are aligned for engagement with pinion grooves 214a and 214b.

Figure 10:
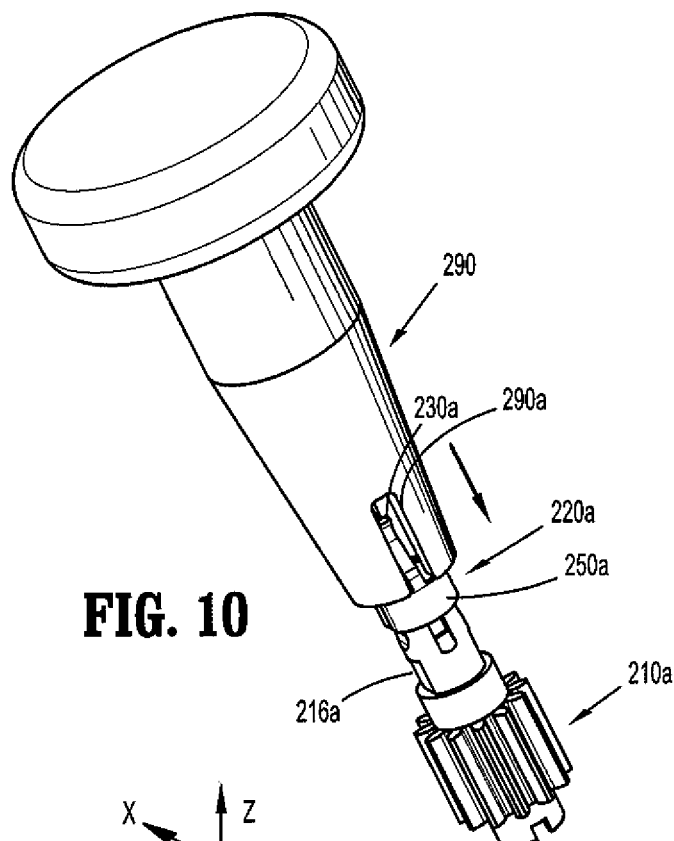
FIG. 10 is a perspective view of the pinion clip of FIG. 8 in which a driving tool used to force the pinion clip to its final resting position about the pinion.

As seen in FIG. 10, an insertion tool 290 can be used to fit pinion clip 220a about pinion 210a. The insertion tool 290 is shown here having receiving slots 290a and 290b (hidden from view) for accommodating pinion clip arms 230a, 230b of pinion clip 220a during connection of pinion clip 220a to pinion 210a such that a distal surface of the insertion tool 290 directly engages the collar 250a. In use, insertion tool 290 is advanced relative to pinion 210a, so as to advance pinion clip 220a over and along pinion 210a.

Figure 11:
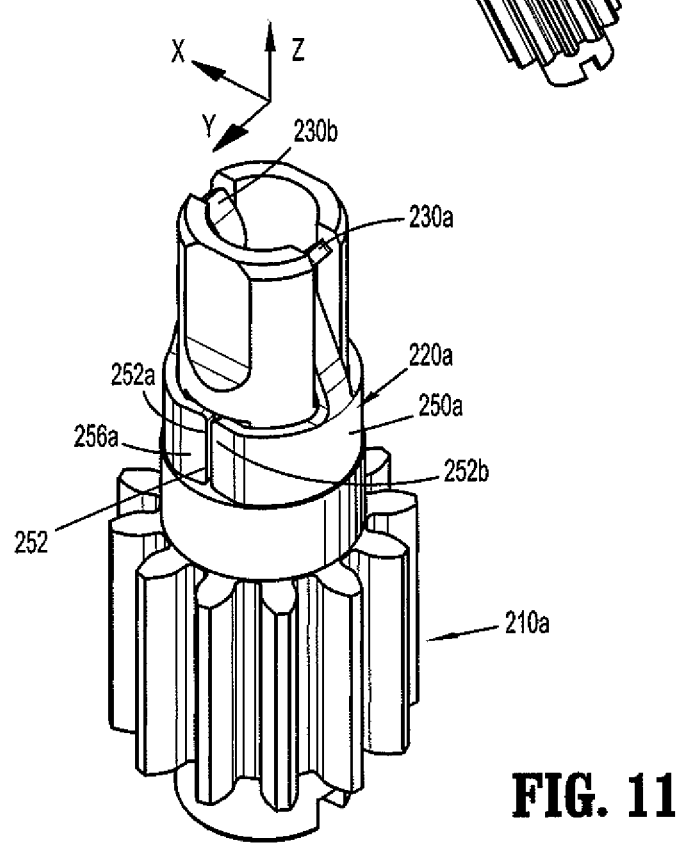
FIG. 11 is a perspective view of the pinion clip of FIG. 8, assembled with the pinion.

Turning now to FIG. 11, the pinion clip 220a is shown in its final resting position about pinion 210a. In the final resting position, flat 256a of collar 250 is shown in engagement with the receiving surface or flat 216a of pinion 210a, with flat 256a of pinion clip 220a beneath a lip 218a defined by flat 216a of pinion 210a, and the pinion clip arms 230a and 230b are in engagement with pinion grooves 214a and 214b, respectively. Thus, the pinion clip 220a is secured about the pinion 210a, and is restricted from at least rotation about a central rotational axis of pinion 210a and distal movement along pinion 210a. When secured to pinion 210a, the gooseneck portions of pinion clip arms 230a, 230b are configured and dimensioned so as to project radially inward from an inner surface or beyond an inner surface of the bore 212a of pinion 210a so as to engage a drive shaft 200 that is connected to pinion 210a.

Figure 12:
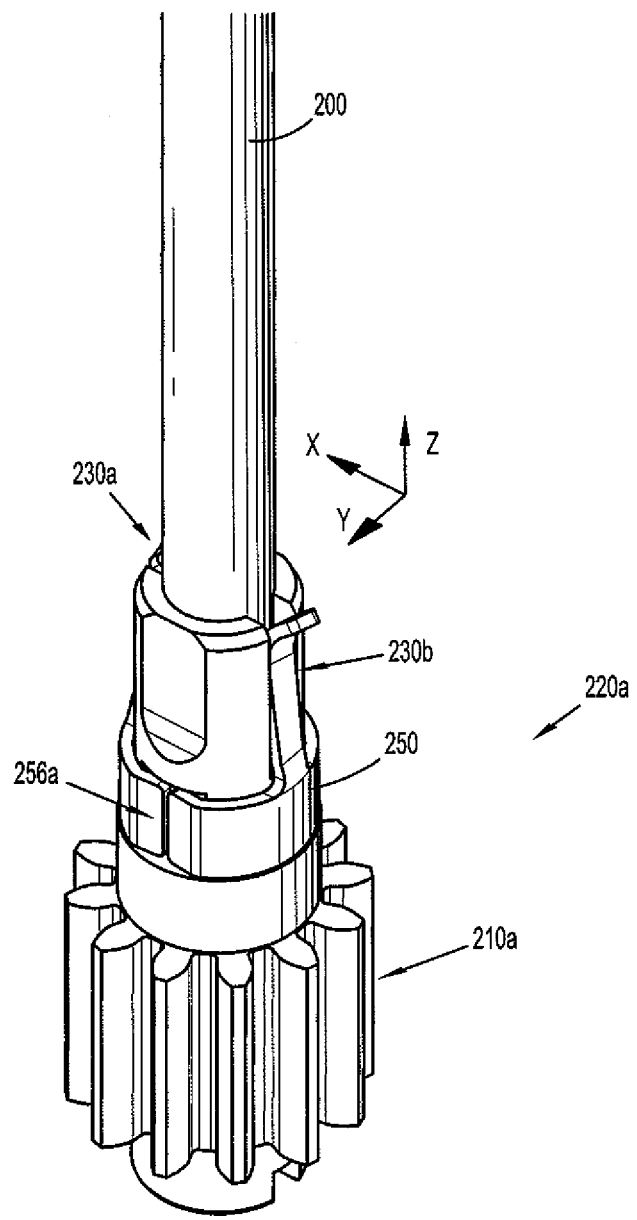
FIG. 12 is a perspective view of the pinion clip of FIG. 8, fully assembled with the pinion and drive shaft.

As seen in FIG. 12, a final assembly of the pinion clip 220a on the pinion 210a is shown, together with the engagement of drive shaft 200. Pinion clip arms 230a, 230b engage drive shaft 200 in a manner identical to or substantially similar to the manner in which pinion clip arms 130a, 130b engage drive shaft 200, as described in detail above.

Figure 13:
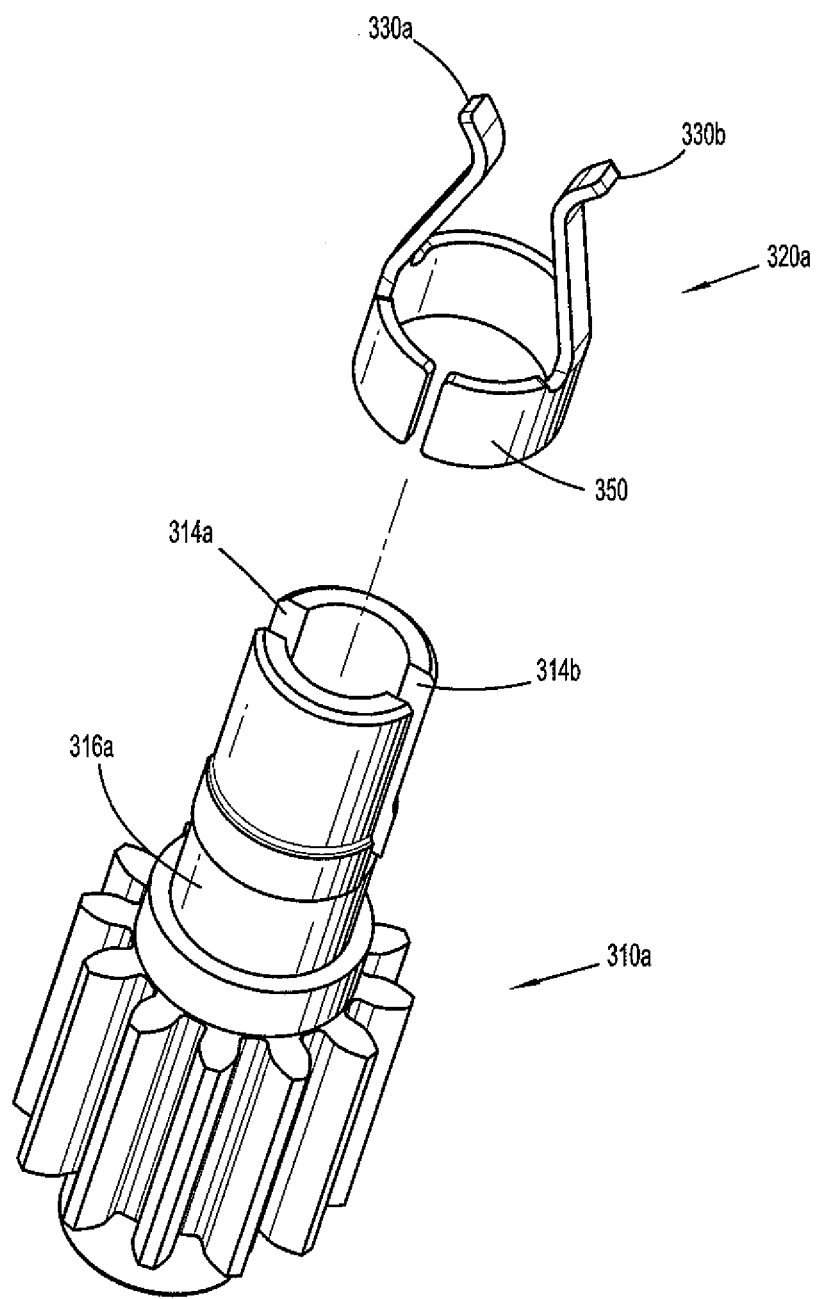
FIG. 13 is a perspective view of an embodiment of a pinion clip including a collar tab for surface engagement, aligned for placement on the pinion.
Figure 14:
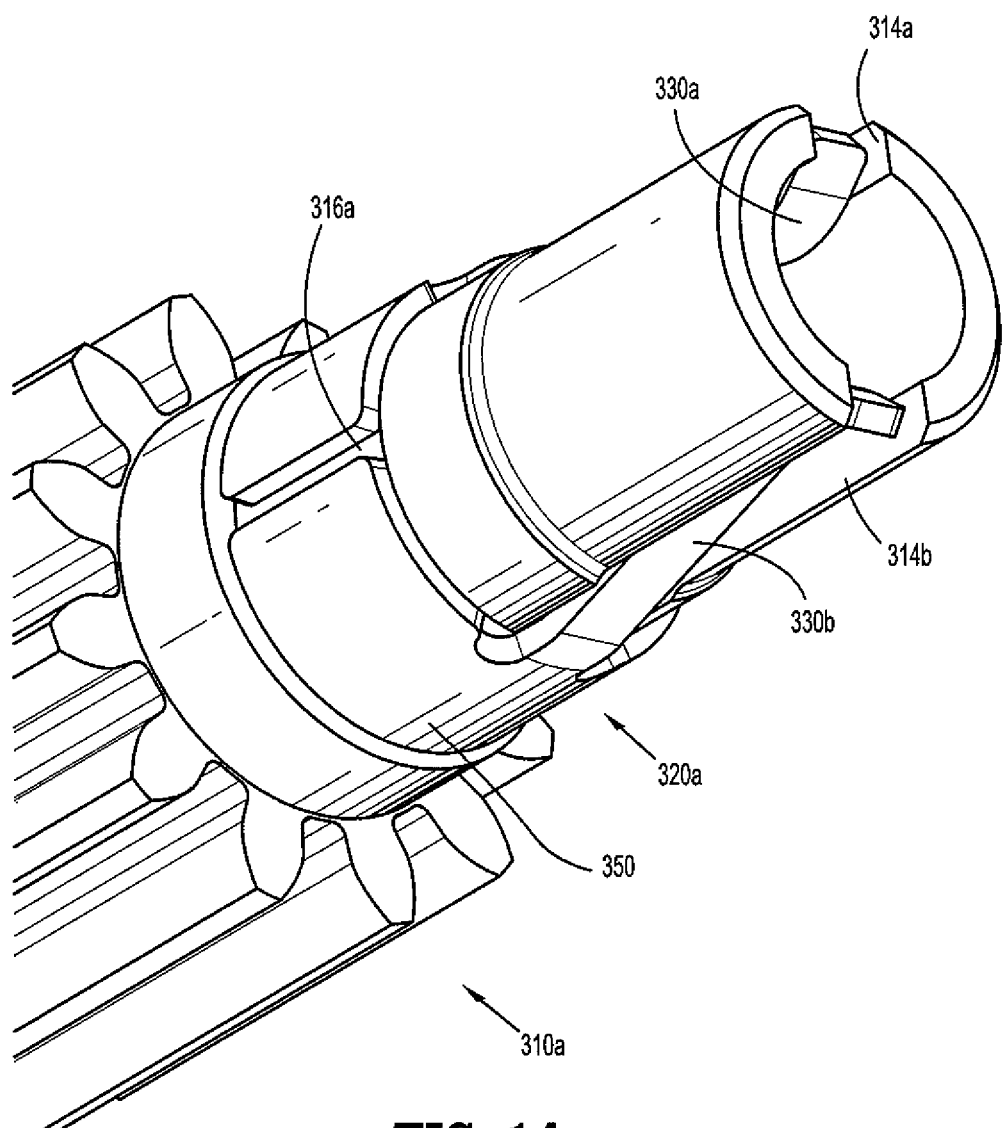
FIG. 14 is a perspective view of the pinion clip of FIG. 13, assembled on the pinion.
Figure 15:
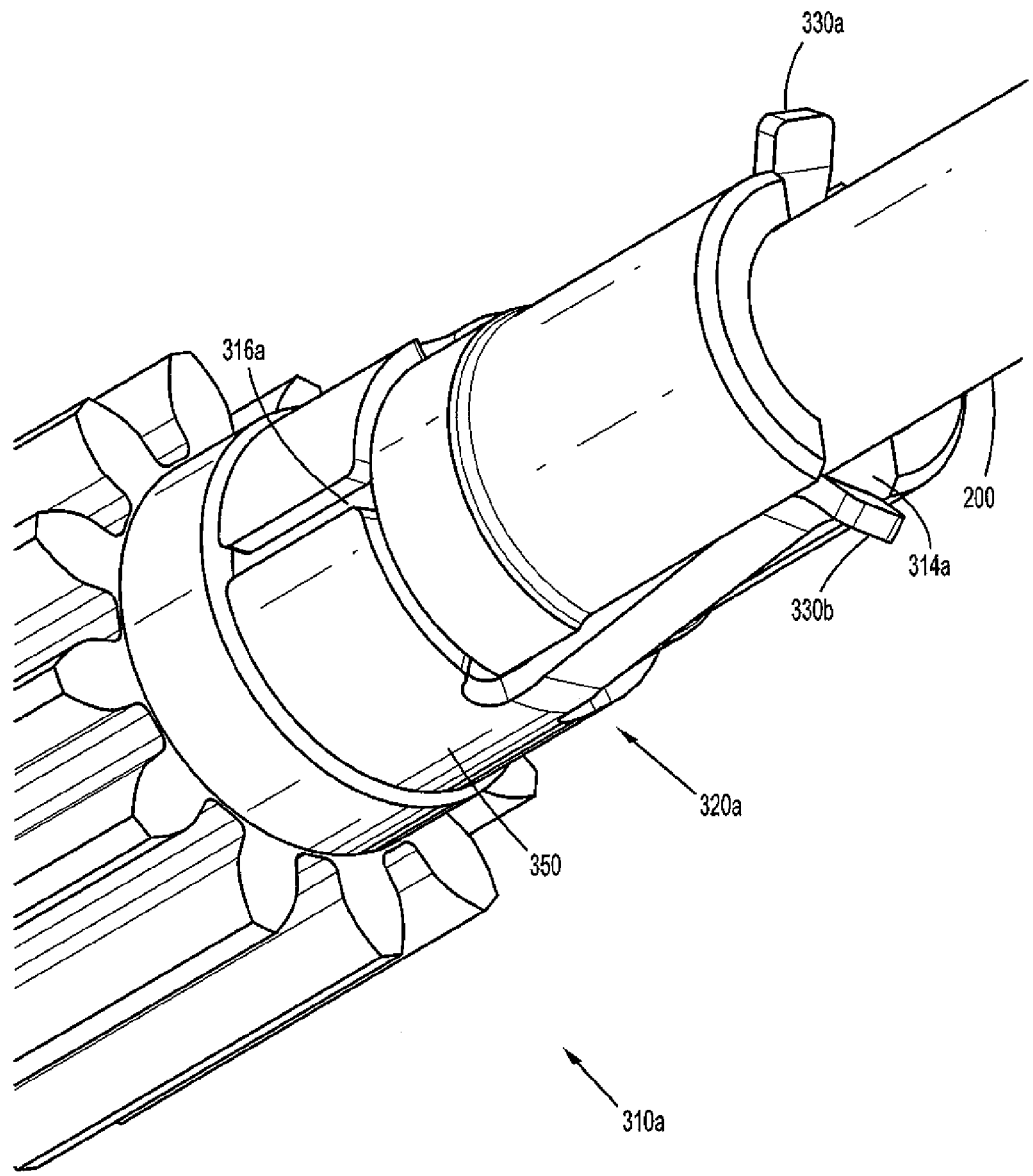
FIG. 15 is a perspective view of the pinion clip of FIG. 13, fully assembled with the pinion and drive shaft.

Turning now to FIGS. 13-15, an embodiment of another pinion clip 320a is shown, and is substantially similar to pinion clip 220a. Pinion clip 320a includes a collar 350 substantially similar to collar 250 of pinion clip 220a. In contrast to collar 250, collar 350 is entirely circular, devoid of any flat as provided in collar 250 of pinion clip 220a. Collar 350 is configured to be seated in an annular race 316a defined in an outer surface of pinion 310. In this embodiment, engagement of the goose-neck portions of pinion clip arms 330a, 330b of pinion clip 310a in pinion grooves 314a, 314b of pinion 310a prevents at last rotation of the pinion clip 320a about the central rotational axis of pinion 310a Referring to FIG. 14, a final resting position of pinion clip 320a about the pinion 310a is shown. As seen in FIG. 14, collar 350 is shown deposed within the annular race 316a defined in the outer surface of pinion 310. Also as illustrated in FIG. 14, the pinion clip arms 330a, 330b are shown disposed within respective pinion grooves 314a, 314b.

As seen in FIG. 15, a final assembly of pinion clip 320a, on the pinion 310a is shown together with the engagement of drive shaft 200. Pinion clip arms 330a, 330b engage drive shaft 200 in a manner identical to or substantially similar to the manner in which pinion clip arms 130a, 130b engage drive shaft 200, as described in detail above.

Referring to FIGS. 16-19, yet another embodiment of a pinion clip 420a is shown. Pinion clip 420a includes a pair of pinion clip arms 430a, 430b extending from a base member 450 in the form of a U-shaped stem having a pair of legs 450a, 450b. Each leg 450a, 450b defines an aperture 452a, 452b therein that is juxtaposed with respect to one another. Pinion clip arms 430a, 430b extend from a respective leg 450a, 450b in such a manner so as to define a respective outwardly projecting shoulder 454a, 454b.

Figure 16:
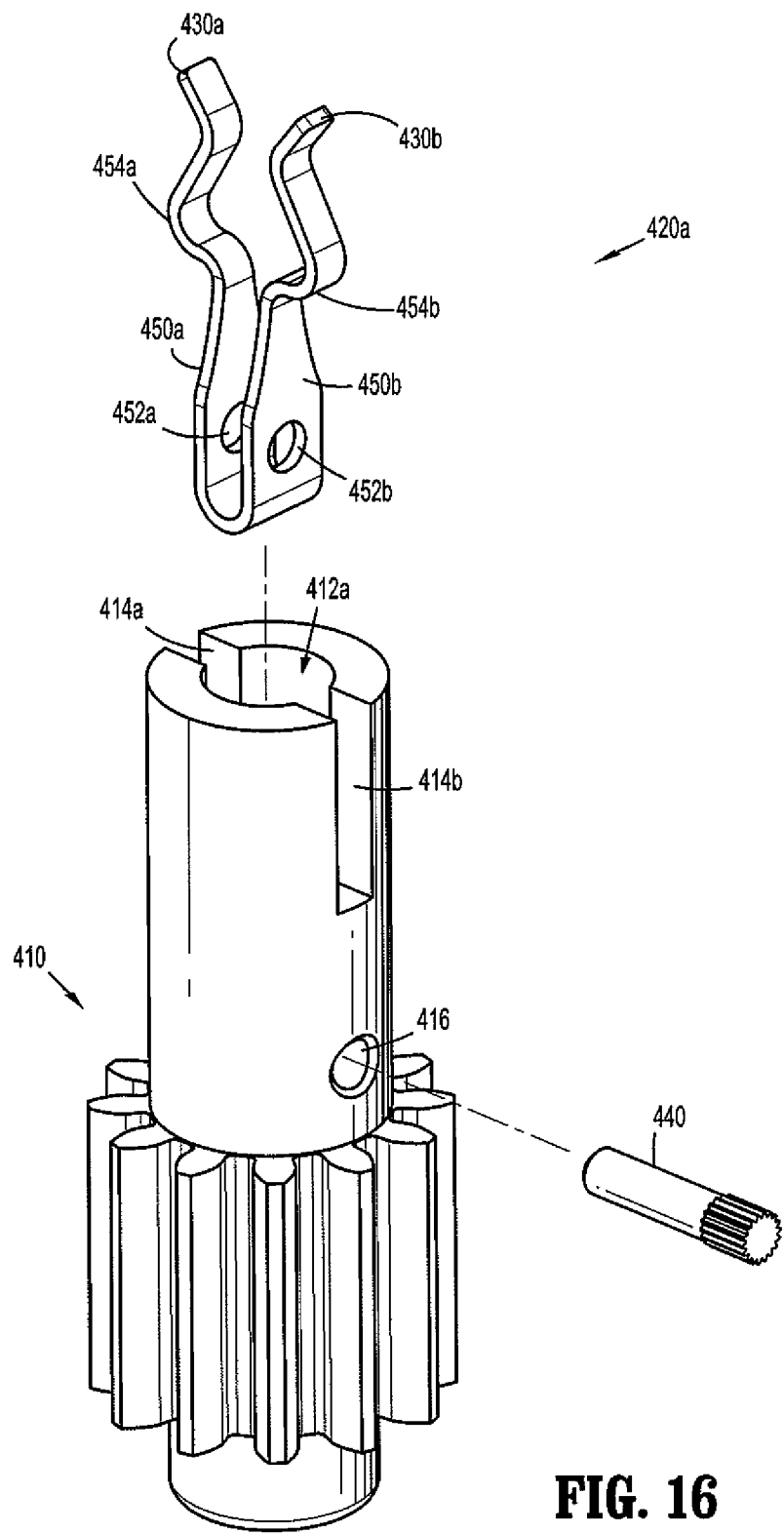
FIG. 16 is a cross-sectional view of an embodiment of a pinion clip in which the pinion clip is slotted for receiving a locking pin, the pinion clip and locking pin aligned for placement in the pinion.

With continued reference to FIG. 16, pinion 410a defines an aperture 416 extending radially therethrough. Aperture 416 is axially located along pinion 410a such that apertures 452a, 452b of legs 450a, 450b of base member 450 align therewith when pinion clip 420a is seated with the bore 412a of pinion 410a. Pinion 410a further includes a locking pin 440 sized for insertion into and through aperture 416 of pinion 410a and apertures 452a, 452b of pinion clip 410a. With pinion clip 420a seated in pinion 410a and with pin 440 extending through aperture 416 thereof and through apertures 452a, 452b, pin 440 is used to secure pinion clip 420a to pinion 410a.

Figure 17:
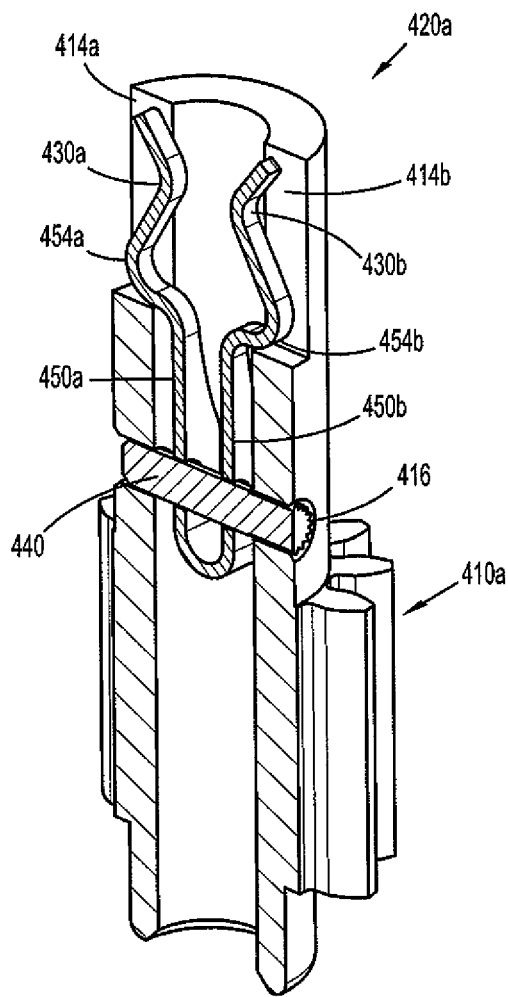
FIG. 17 is a cross-sectional view of the pinion clip of FIG. 16, in which the pinion clip and locking pin are assembled with the pinion.
Figure 18:
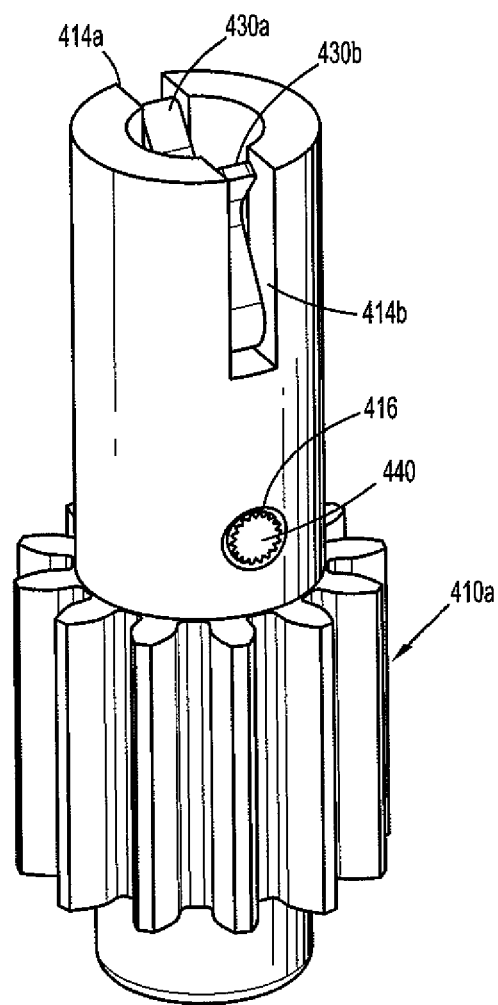
FIG. 18 is a perspective view of the pinion clip of FIG. 16, in which the pinion clip and locking pin are assembled with the pinion.

Turning now to FIGS. 17 and 18, pinion clip 420a is shown connected to pinion 410a. Here, the locking pin 440 is shown extending through pinion 410a and legs 450a, 450b of pinion clip 420a to secure the pinion clip 420a in place in pinion 410a. The shoulders 454a, 454b between pinion clip arms 430a, 430b and legs 450a, 450b rest upon ridges or ledges which are formed at the base portion of pinion grooves 412a, 412b, as shown.

Figure 19:
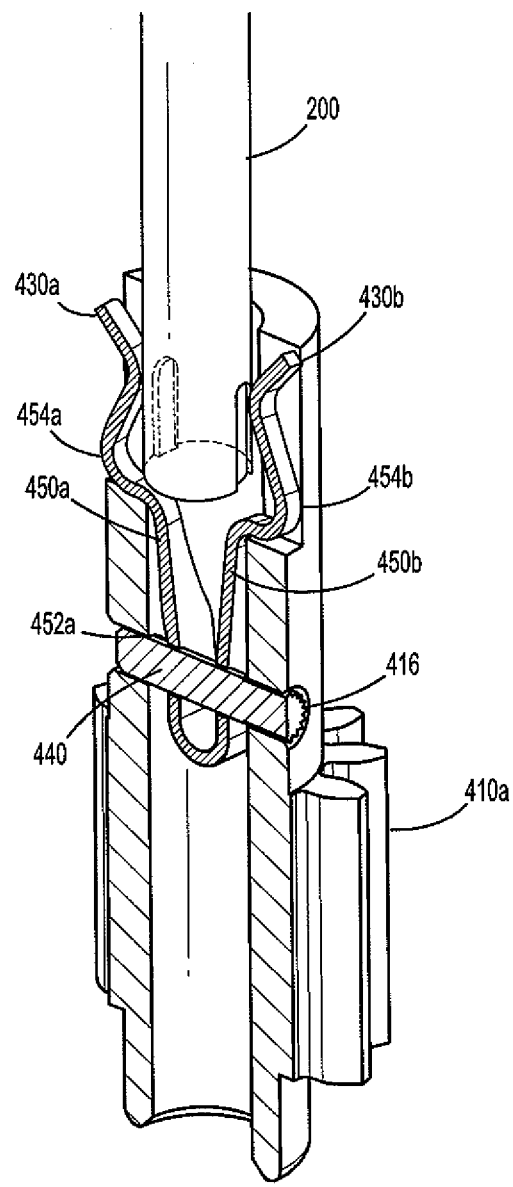
FIG. 19 is a perspective view of the pinion clip of FIG. 17, in which the pinion clip and locking pin are fully assembled with the pinion and drive shaft.

As seen in FIG. 19, the complete assembly of the pinion clip 420a within the pinion 410a is shown. In particular, the pinion clip arms 430a and 430b are in engagement with the pinion grooves 414a, 414b, respectively, and locking pin 440 is extending through pinion 410a and legs 454a, 454b of pinion 410. As seen in FIG. 19, pinion clip arms 430a, 430b engage drive shaft 200 in a manner identical to or substantially similar to the manner in which pinion clip arms 130a, 130b engage drive shaft 200, as described in detail above.

In accordance with the present disclosure, it is contemplated that a pinion clip may have one, two, or more than two arms, and that these arms may or may not have one or more bends for engagement with surfaces within or without a pinion. Further, the pinion clip arm(s) may lack bends altogether in embodiments.

It is contemplated that any of the pinion clips provided herein may be coated with a finishing material that enhances the frictional surface engagement between pinion clip arms and drive shaft.

It is further contemplated that other embodiments of a pinion clip incorporating a collar may employ other methods such as press fit to maintain an attachment to a pinion.

It is additionally contemplated that other embodiments of a pinion clip incorporating a collar may incorporate shaped surfaces on the interior circumference of the collar for engagement with a receiving surface on the outer circumference of a pinion.

It is also contemplated that other embodiments of a pinion clip may be constructed so as to accommodate non-circular drive shafts.

It will be understood that various modifications may be made to the embodiments of the presently disclosed coupling clip assemblies. Therefore, the above description should not be construed as limiting, but merely as exemplifications of embodiments. Those skilled in the art will envision other modifications within the scope and spirit of the present disclosure.

What is claimed is:

1. A pinion clip operable with a drive shaft and pinion assembly, the pinion clip configured to engage a pinion defining a longitudinal axis and having an internal bore, the pinion clip comprising:
   two arms adapted to be disposed along the longitudinal axis of the pinion; and
   a base member defining a base axis and two base posts, the base axis in perpendicular orientation to the longitudinal axis of the pinion, and the base member further defining an aperture centrally disposed thereon such that the two base posts are in opposed relation to each other along an axis defined by the aperture;
   wherein the pinion clip is adapted to be positioned on the pinion such that the two arms are adapted to intersect a diameter of the internal bore of the pinion; and
   wherein the two base posts of the base member are adapted to secure the pinion clip to the pinion.

2. The pinion clip of claim 1, wherein each arm forms a goose-neck configuration such that a distal end of each arm extends away from the longitudinal axis defined by the pinion.

3. The pinion clip of claim 1, wherein the two base posts are insertable into apertures of the pinion to secure the pinion clip to the pinion.

4. A pinion and pinion clip assembly configured for selective coupling with a rotatable drive shaft, the pinion and pinion clip assembly comprising:
   a pinion being a substantially cylindrical member, the pinion having proximal and distal ends and defining a longitudinal axis and an internal bore;
   a pinion clip configured for connection to the pinion, the pinion clip including two arms adapted to be disposed along the longitudinal axis of the pinion and a base member defining a base axis and two base posts, the base axis in perpendicular orientation to the longitudinal axis of the pinion, and the base member further defining an aperture centrally disposed thereon such that the two base posts are in opposed relation to each other along an axis defined by the aperture;

wherein the pinion clip is adapted to be positioned on the pinion such that the two arms are adapted to intersect a diameter of the internal bore of the pinion; and wherein the two base posts of the base member are adapted to secure the pinion clip to the pinion.

5. The pinion and pinion clip assembly of claim 4, wherein the pinion includes at least one pinion groove formed in an outer surface thereof and being configured to receive the two base posts of the base member of the pinion clip to secure the pinion clip to the pinion.

6. The pinion and pinion clip assembly of claim 4, wherein each arm forms a goose-neck configuration such that a distal end of each arm extends away from the longitudinal axis defined by the pinion.

7. The pinion and pinion clip assembly of claim 4, wherein the two base posts extend away from the two arms.

* * * * *